(12) United States Patent
Ullrich et al.

(10) Patent No.: US 12,262,909 B2
(45) Date of Patent: Apr. 1, 2025

(54) ELECTROSURGICAL INSTRUMENT

(71) Applicant: Creo Medical Limited, Monmouth (GB)

(72) Inventors: George Christian Ullrich, Angelsey (GB); David Edward Webb, Bangor (GB); Christopher Paul Hancock, Chepstow (GB); Malcolm White, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 0 days.

(21) Appl. No.: 18/718,746

(22) PCT Filed: Dec. 14, 2022

(86) PCT No.: PCT/EP2022/085964
§ 371 (c)(1),
(2) Date: Jun. 11, 2024

(87) PCT Pub. No.: WO2023/117649
PCT Pub. Date: Jun. 29, 2023

(65) Prior Publication Data
US 2024/0415532 A1 Dec. 19, 2024

(30) Foreign Application Priority Data
Dec. 24, 2021 (GB) .................................... 2119001

(51) Int. Cl.
*A61B 17/3203* (2006.01)
*A61B 17/00* (2006.01)

(52) U.S. Cl.
CPC .... *A61B 17/3203* (2013.01); *A61B 17/00234* (2013.01); *A61B 2017/00225* (2013.01);
(Continued)

(58) Field of Classification Search
CPC .......... A61B 17/3203; A61B 17/00234; A61B 2017/00225; A61B 2017/00296;
(Continued)

(56) References Cited

U.S. PATENT DOCUMENTS

| | | |
|---|---|---|
| 2011/0208185 A1 | 8/2011 | Diamant et al. |
| 2012/0310228 A1 | 12/2012 | Bonn et al. |

(Continued)

FOREIGN PATENT DOCUMENTS

| | | |
|---|---|---|
| CN | 110946643 A | 4/2020 |
| WO | WO 00/28908 A1 | 5/2000 |
| WO | WO 2020/104419 A1 | 5/2020 |

OTHER PUBLICATIONS

International Preliminary Report on Patentability, issued by the International Preliminary Examining Authority in corresponding International Patent Application No. PCT/EP2022/085964, dated Mar. 21, 2024.

(Continued)

*Primary Examiner* — Mohamed G Gabr
(74) *Attorney, Agent, or Firm* — ArentFox Schiff LLP

(57) ABSTRACT

An electrosurgical instrument for delivering pressurised fluid to a biological tissue, and for delivering radiofrequency electromagnetic energy and/or microwave frequency EM energy to the biological tissue. The electrosurgical instrument comprises a flexible shaft with an instrument tip connected to its distal end. The instrument tip comprises a planar body made of a first dielectric material separating a first conductive element from a second conductive element, for delivering EM energy to the biological tissue. The instrument tip has a nozzle for delivering the pressurised fluid directly to the biological tissue. An outer sleeve extends over the flexible shaft and a proximal section of the instru- (Continued)

ment tip to reinforce the flexible shaft and a junction between the flexible shaft and instrument tip.

16 Claims, 13 Drawing Sheets

(52) U.S. Cl.
CPC ............... *A61B 2017/00296* (2013.01); *A61B 2017/00477* (2013.01); *A61B 2017/00526* (2013.01); *A61B 2017/00544* (2013.01); *A61B 2017/00836* (2013.01); *A61B 2017/00862* (2013.01); *A61B 2017/00929* (2013.01)

(58) Field of Classification Search
CPC .......... A61B 2017/00477; A61B 2017/00526; A61B 2017/00544; A61B 2017/00836; A61B 2017/00862; A61B 2017/00929
See application file for complete search history.

(56) References Cited

U.S. PATENT DOCUMENTS

| | | |
|---|---|---|
| 2015/0196353 A1* | 7/2015 | Hancock .............. A61B 18/042 606/46 |
| 2015/0313666 A1 | 11/2015 | Aljuri et al. |
| 2016/0120588 A1 | 5/2016 | Amoah et al. |
| 2018/0250057 A1 | 9/2018 | Cosmescu |
| 2018/0318459 A1 | 11/2018 | Hancock et al. |
| 2020/0268445 A1* | 8/2020 | Hancock ............ A61B 18/1815 |

OTHER PUBLICATIONS

International Search Report and Written Opinion, issued by the International Searching Authority in corresponding International Patent Application No. PCT/EP2022/085964, dated Mar. 27, 2023.
Search Report Under Section 17(5), issued by the United Kingdom Intellectual Property Office in corresponding United Kingdom Application No. GB2119001.2, dated May 31, 2022.
Written Opinion, issued by the International Preliminary Examining Authority in corresponding International Patent Application No. PCT/EP2022/085964, dated Jun. 9, 2023.

* cited by examiner

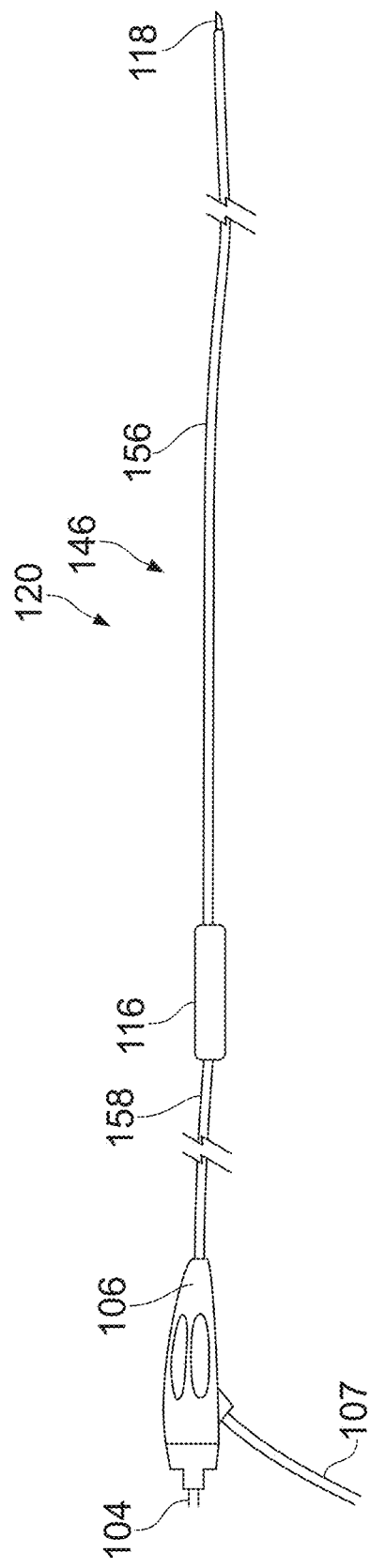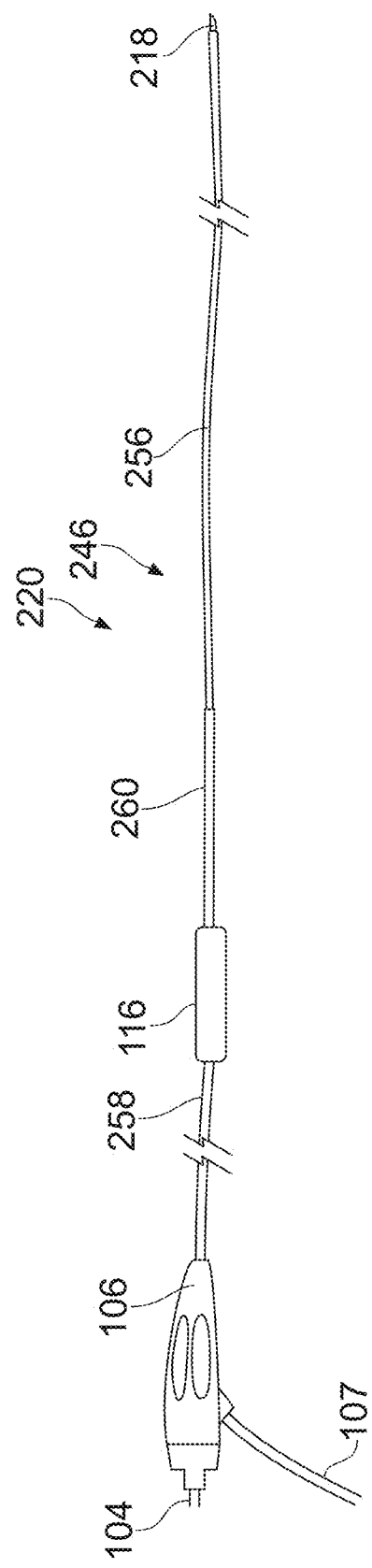

ELECTROSURGICAL INSTRUMENT

CROSS-REFERENCE TO RELATED APPLICATIONS

This application is a National Stage Entry of International Application No. PCT/EP2022/085964, filed Dec. 14, 2022, which claims priority to United Kingdom Patent Application No. 2119001.2, filed Dec. 24, 2021. The disclosures of the priority applications are hereby incorporated in their entirety by reference.

FIELD OF THE INVENTION

The present invention relates to a surgical instrument for injecting pressurised fluid into tissue. The surgical instrument may be an electrosurgical instrument for delivering electromagnetic energy (e.g. radiofrequency and/or microwave frequency energy) into biological tissue for cutting tissue and/or for haemostasis (i.e. promoting blood coagulation). For example, the invention may be applied to instruments sized to be suitable for insertion through the instrument channel of a standard surgical endoscope.

BACKGROUND

Surgical resection is a means of removing sections of organs from within the human or animal body. Such organs may be highly vascular. When tissue is cut (divided or transected) small blood vessels called arterioles are damaged or ruptured. Initial bleeding is followed by a coagulation cascade where the blood is turned into a clot in an attempt to plug the bleeding point. During an operation, it is desirable for a patient to lose as little blood as possible, so various devices have been developed in an attempt to provide blood free cutting. For endoscopic procedures, bleeds are also undesirable, and need to be dealt with in an expedient manner, since the blood flow may obscure the operator's vision, which may prolong surgery and potentially lead to the procedure needing to be terminated and another method used instead, e.g. open surgery.

Electrosurgical generators are prevalent in hospital operating theatres, often for use in open and laparoscopic procedures, and increasingly for use with surgical scoping devices, e.g. an endoscope or the like. In endoscopic procedures the electrosurgical accessory is typically inserted through a lumen inside an endoscope. Considered against the equivalent access channel for laparoscopic surgery, such a lumen is comparatively narrow in bore and greater in length.

Instead of a sharp blade, it is known to use radiofrequency (RF) energy to cut biological tissue. The method of cutting using RF energy operates using the principle that as an electric current passes through a tissue matrix (aided by the ionic contents of the cells and the intercellular electrolytes), the impedance to the flow of electrons across the tissue generates heat. In practice, an instrument is arranged to apply an RF voltage across the tissue matrix that is sufficient to generate heat within the cells to vapors the water content of the tissue. However, as a result of this increasing desiccation, particularly adjacent to the RF emitting region of the instrument (which has the highest current density of the current path through tissue), direct physical contact between the tissue and instrument can be lost. The applied voltage then manifests itself as a voltage drop across this small void, which causes ionisation in the void that leads to a plasma. Plasma has a very high volume resistivity compared with tissue. The energy supplied to the instrument maintains the plasma, i.e. completes the electrical circuit between the instrument and the tissue. Volatile material entering the plasma can be vaporised and the perception is therefore of a tissue dissecting plasma. GB 2 523 246 describes an electrosurgical instrument for applying to biological tissue RF electromagnetic energy and/or microwave frequency EM energy. The instrument comprises a shaft insertable through an instrument channel of a surgical scoping device. At a distal end of the shaft there is an instrument tip comprising a planar transmission line formed from a sheet of a first dielectric material having first and second conductive layers on opposite surfaces thereof. The planar transmission line is connected to a coaxial cable conveyed by the shaft. The coaxial cable is arranged to deliver either microwave or RF energy to the planar transmission line. The coaxial cable comprises an inner conductor, an outer conductor coaxial with the inner conductor, and a second dielectric material separating the outer and inner conductors, the inner and outer conductors extending beyond the second dielectric at a connection interface to overlap opposite surfaces of the transmission line and electrically contact the first conductive layer and second conductive layer respectively. The instrument further comprises a protective hull with a smoothly contoured convex undersurface facing away from the planar transmission line. The undersurface comprises a longitudinally extending recessed channel formed therein. A retractable needle is mounted within the instrument, and operable to extend through the recessed channel to protrude from a distal end of the instrument. The needle can be used to inject fluid into a treatment zone before the RF or microwave energy is applied.

The present invention has been devised in light of the above considerations.

SUMMARY OF THE INVENTION

The present invention provides a development to the concept discussed in GB 2 523 246.

It would be desirable to reduce the size of the instrument, e.g. by making it thinner and/or shorter. A compact arrangement may provide several advantages. For example, a compact arrangement may allow the instrument to be used within narrower scoping devices and/or in smaller biological structures, may enable the instrument to be more easily maneuvered, and/or may help to improve the control and precision at the instrument tip.

However, it is difficult to reduce the size of the instrument whilst retaining its functionality.

For example, the ability to reduce the instrument size is limited by the size of the retractable needle and its associated structures (e.g. the contoured undersurface of the protective hull). One option would be to try to reduce the size of the needle. However, it is difficult to reduce the size to a significant extent whilst still maintaining the ability to deliver an effective amount of fluid at an appropriate rate. Additionally, a smaller needle may be more easily clogged or obstructed e.g. if attempting to apply a relatively viscous fluid to a treatment zone. The inventors have thus sought to develop a system which can omit the retractable needle altogether, to reduce the size of the instrument. However, it is difficult to do so, since the needle provides the function of enabling fluid to be delivered to the treatment site, i.e. by piercing tissue (e.g. mucosa and/or submucosa) before injecting fluid into it. By injecting fluid in this manner, the treatment zone can be plumped to form a bulge which can then be cut more easily (compared to an un-injected treatment zone with a relatively lower profile), e.g. by forming cuts around the base of the bulge to remove tissue above it.

At its most general, the inventors have developed a system which is capable of utilising a high-pressure fluid, rather than a needle, to puncture tissue. However, it can be difficult to convey high-pressure fluid through the instrument without the high-pressure fluid damaging the instrument (e.g. by causing it to burst) or affecting the movement of the instrument (e.g. by affecting its rotation/bending). Additionally, it is difficult to address these problems (e.g. by making the instrument stronger and more robust) whilst still maintaining a small instrument size.

The inventors have developed modified instruments which are suitable for conveying high-pressure fluid to a treatment site to pierce tissue. The modified instruments can advantageously be more compact than those of the prior art, whilst also being more robust to withstand the high pressures exerted by the fluid. A first aspect of the invention provides a surgical instrument (e.g. an electrosurgical instrument) for delivering pressurised fluid to a biological tissue, the surgical instrument comprising: a flexible shaft having a first fluid channel for conveying the pressurised fluid; an instrument tip connected to a distal end of the flexible shaft, the instrument tip having a second fluid channel for receiving the pressurised fluid from the first fluid channel, wherein the second fluid channel comprises a nozzle at a distal end thereof for delivering the pressurised fluid directly to the biological tissue; and an outer sleeve extending over the flexible shaft and a proximal section of the instrument tip to reinforce the flexible shaft and a junction between the flexible shaft and instrument tip.

Advantageously, the surgical instrument may use pressurised fluid to inject fluid directly into tissue from a nozzle, rather than requiring a needle to convey the fluid into the tissue. For example, the fluid pressure is sufficiently high to pierce or penetrate through biological tissue (e.g. mucosa tissue and/or submucosa tissue). Alternatively, the pressurised fluid may be used to perfuse or lift tissue in an area which has already been pierced (e.g. by another instrument or another needle on the surgical instrument which is not connected to the second fluid channel).

The flexible shaft may include a cannula tube having a lumen for transporting fluid. In order to provide a torque transfer function, the cannula tube may be formed of a braided tube, e.g. comprising a braided wire (e.g. stainless steel) wrap mounted between a radially inner polymer layer and a radially outer polymer layer, wherein the polymer may be e.g. Pebax®. Alternatively, the cannula tube may be formed of a coiled tube, e.g. an Asahi® Torque Coil. Such arrangements may be particularly prone to stretching under the force of fluid pressure.

Because the outer sleeve extends over the flexible shaft, it can help to reinforce an outer surface of the shaft to help prevent the flexible shaft from deforming (e.g. expanding, stretching, or bursting) as the pressurised fluid travels therethrough. Additionally, because the outer sleeve extends further over the instrument tip, it can help to seal a junction between the flexible shaft and instrument tip, thereby helping prevent relative movement of the flexible shaft relative to the instrument tip and helping prevent leakage of pressurised fluid from the junction. The "outer sleeve" may therefore also be referred to as a "reinforcement sleeve", a "sealing sleeve," or an "encapsulating sleeve".

The second fluid channel may be fixed (e.g. non-retractable) relative to the flexible shaft.

The distal end of the second fluid channel may form the nozzle, that is, the nozzle may be formed integrally with the rest of the second fluid channel.

As used herein, the "nozzle" may be configured to direct a controlled jet of pressurised fluid from the second fluid channel directly into tissue. As used herein, "direct" fluid transfer may refer to an arrangement in which the fluid does not flow through any intermediate structures along its flow path.

The nozzle may be positioned and shaped so as to avoid inadvertently piercing or otherwise damaging tissue. For example, the nozzle may have a relatively blunt or dull (non-sharp) fluid outlet for injecting the pressurised fluid into the tissue. For example, the nozzle may be cylindrical and/or may have a round (e.g. circular) outlet. The nozzle may be fixed (e.g. non-retractable) with respect to the flexible shaft. The nozzle may have an aperture that is flush with a surface of the instrument tip (e.g. a distal surface of the instrument tip) or is located proximal to a distal surface of the instrument tip, so as not to protrude from the instrument.

Since the second fluid channel comprises a nozzle at a distal end thereof for delivering the pressurised fluid directly to the biological tissue, the instrument may not require a retractable needle for piercing the biological tissue and conveying the fluid from the second fluid channel into the biological tissue. Further, the flexible shaft may not require a push rod, control wire, or other means for controlling deployment of such a retractable needle at the second fluid channel. The instrument may therefore have a relatively simpler configuration and smaller profile than instruments requiring a retractable needle.

As used herein, the phrase "needle" may refer to a tube (e.g. metallic tube) having a sharp point at its distal end for piercing tissue. A "retractable needle" may be longitudinally movable relative to a flexible sheath between a stowed configuration and a deployed configuration, e.g. by using control means such as a push rod which extends through the flexible sheath to the needle. When in the stowed configuration, a sharp distal end of the retractable needle may be located proximally to a distal end of the instrument tip, so as not to protrude from the instrument tip. When in the deployed configuration, the sharp distal end may protrude from the instrument tip to pierce the tissue.

Optionally, the instrument tip may not include any retractable needle whatsoever for piercing biological tissue. Optionally, the flexible shaft may also not include any retractable needle for piercing tissue. Further optionally, the instrument tip may not include any needle whatsoever for piercing biological tissue. Further optionally, the flexible shaft may also not include any needle for piercing tissue. Alternatively, in some embodiments, the instrument (e.g. instrument tip or flexible shaft) may include a retractable needle, but the retractable needle may not be connected to the second fluid channel to deliver fluid from the second fluid channel into biological tissue. For example, in some embodiments, the instrument may include a retractable needle which is (solely) used to pierce tissue. The second fluid channel may then be used to inject the already-pieced tissue with pressurised fluid without requiring a needle to do so. In some embodiments, the flexible shaft may include the separate retractable needle, which may then pass through the instrument tip (only) when in a deployed state.

According to the first aspect, the surgical instrument is an electrosurgical instrument for delivering electromagnetic (EM) energy into tissue. In particular, the surgical instrument is an electrosurgical instrument for applying to biological tissue radiofrequency (RF) EM energy and/or microwave frequency EM energy, wherein the instrument tip comprises a planar body made of a first dielectric material separating a first conductive element on a first surface thereof from a second conductive element on a second surface thereof, the second surface facing in the opposite direction to the first surface; wherein the flexible shaft further comprises a coaxial feed cable comprising an inner conductor, an outer conductor coaxial with the inner conductor, and a second dielectric material separating the inner and outer conductors, the coaxial feed cable being for conveying an RF signal and/or microwave signal; and wherein the inner conductor is electrically connected to the first conductive element and the outer conductor is electrically connected to the second conductive element to enable the instrument tip to receive the RF signal and/or the microwave signal.

The instrument may therefore advantageously provide a dual functionality for treating tissue, both by using high-pressure fluid and by using an EM signal. The pressurised fluid may be used to pierce tissue and/or inject fluid into the tissue, and the RF and/or microwave signal may be used to cut the tissue and/or cause haemostasis.

This arrangement may help to prevent the electrosurgical instrument from deforming under high pressures, for similar reasons as discussed above. Further, the outer sleeve may help better protect the electrical connection between the flexible shaft and instrument tip, by encapsulating and sealing an electrical junction between these components.

Optionally, the outer sleeve (e.g. a shrink-fit layer of the outer sleeve) may extend over at least a proximal portion of the instrument tip's planar body. For example, the outer sleeve may extend over 20% or more of the length of the instrument tip's planar body, more preferably over 30% or more of the length of the planar body, more preferably 40% or more of the length of the planar body. Accordingly, the outer sleeve may extend to a central region of the instrument tip. By increasing the extension of the outer sleeve layer, the strength of its adhesion to the instrument tip may be increased, thereby helping to better grip onto the instrument and prevent deformation.

The outer sleeve may therefore include a distal retention portion having a shape and/or size that is different from (e.g. smaller than) a more proximal portion of the outer sleeve (e.g. a portion extending over a distal end of the flexible shaft). For example, the outer sleeve may have a distal retention portion having a planar shape, whereas a more proximal portion of the outer sleeve may have a circular shape having a larger diameter than a thickness of the distal retention portion. These arrangements may help the outer sleeve to grip onto the instrument tip and prevent movement of the instrument tip relative to the flexible shaft. The improved grip may help to prevent longitudinal distortion of the instrument, by helping prevent the flexible shaft or instrument tip from being longitudinally stretched or propelled distally under the force of the pressurised fluid (which could be particularly at risk of occurring e.g. if the flexible shaft comprises a coiled or braided construction). In turn, these arrangements may also help reduce the risk of leakage between the shaft and instrument tip.

In variant arrangements, the surgical instrument may not be configured for delivering EM energy into tissue, e.g. the surgical instrument may have a sole purpose of delivering pressurised fluid into tissue.

Optionally, the coaxial feed cable further includes an innermost insulating layer, wherein the innermost insulating layer is hollow to form the first fluid channel. Therefore, the first fluid channel may extend through a centre of the coaxial feed cable.

Advantageously, this arrangement may facilitate the delivery of fluid by ensuring that the coaxial cable does not obstruct fluid flow through the shaft. Further, this arrangement may also allow the instrument to be made even more compact, e.g. compared to an arrangement in which the fluid channel and coaxial cable are side-by-side within the flexible shaft.

In variant embodiments, the flexible shaft may carry the fluid directly therein, i.e. the flexible shaft may define the first fluid channel, and the coaxial feed cable may be considered to extend through the first fluid channel. Alternatively, the coaxial feed cable and the first fluid channel may extend side-by-side through the flexible shaft.

Preferably, the instrument includes electrical potting to seal an electrical junction between the coaxial feed cable and the instrument tip, the shrink-fit layer extending over the potting. The electrical potting may comprise an adhesive such as UV curing glue. The potting may further help to prevent moisture ingress causing damage to the electrical junction.

Optionally, the outer sleeve may comprise a shrink-fit layer extending over the flexible shaft and a proximal section of the instrument tip to reinforce the flexible shaft and the junction between the flexible shaft and instrument tip. For example, the shrink-fit layer may extend over a proximal section of the planar body, as discussed above.

Because shrink-fit layers are formed by starting with a sleeve (or tube) that can be slid over the shaft and instrument tip, and then shrinking the sleeve to fit to the shaft and instrument tip, they can provide a tight grip, rendering it very difficult for the shrink-fit layer to subsequently be detached or slid over the instrument. By using a shrink-fit layer, the outer sleeve may conform closely to the surface of the flexible shaft and/or instrument to closely grip onto these surfaces without substantially increasing the size of the instrument. The shrink-fit layer may therefore help to prevent deformation and/or fluid leakage from the modified instrument, to achieve the above-referenced advantages whilst maintaining a relatively small size.

As used herein, the phrase "shrink-fit" may refer to a layer formed of heat shrink materials and/or cold shrink materials. The materials may have insulating properties and may be considered to "mould" to the surface of the flexible shaft.

Preferably, the shrink-fit layer comprises a heat-shrink layer (e.g. formed of a thermoplastic). Advantageously, a heat-shrink layer may allow for improved control of the adherence of the outer sleeve to the shaft, e.g. since the heating temperature can be increased during shrink-fitting to improve the adhesion of the outer sleeve in a particular zone (e.g. near an engagement structure on the flexible shaft and/or instrument tip).

Optionally, the shrink-fit layer comprises fluorinated ethylene propylene (FEP). FEP is a particularly useful heat-shrink material that can help the instrument withstand relatively high pressures whilst maintaining a relatively small profile. For example, a FEP overcoating can be provided to reinforce the instrument, having a thin profile of 50 microns or less, preferably 30 microns or less. Alternatively, the outer sleeve may comprise another shrink-fit material, e.g. polyester shrink material.

Optionally, the outer sleeve extends over the entire length of the flexible shaft. Optionally, the outer sleeve (e.g. the shrink-fit layer and/or an additional stiffening layer) extends beyond a proximal end of the flexible shaft, e.g. to overhang the proximal end of the flexible shaft. The outer sleeve may therefore be used to reinforce a proximal junction between the flexible shaft and a further device (e.g. an interface joint or a fluid delivery apparatus such as a high-pressure syringe) for conveying the pressurised fluid into the flexible shaft. This arrangement may help to prevent deformation and/or fluid leakage at the proximal end of the flexible shaft, as well as along the entire length of the flexible shaft and at the distal junction with the instrument tip.

As used herein, a "proximal" region of the outer sleeve refers to a region located away from the instrument tip, e.g. near a pressurised fluid delivery device (e.g. syringe). Conversely, a "distal" region of the outer sleeve refers to a region located closer to the instrument tip.

Optionally, the outer sleeve is configured to increase in thickness toward a proximal region of the instrument. The instrument may include a distal portion for extending through a scoping device in use, and a remaining portion having a wider diameter for being outside the scoping device in use. By providing a greater diameter in the proximal region of the outer sleeve (which may be outside of the scoping device when in use), the instrument may be stiffer to provide better rotational control in this region, e.g. by reducing the risk that the shaft may coil up outside of the scoping device. Further, by providing a smaller diameter in the distal region of the outer sleeve, these benefits may be maintained whilst also allowing the instrument to be inserted through a relatively small scoping device and easing maneuverability of the instrument tip around the target tissue. Accordingly, the provision of a variable diameter along the length of the outer sleeve may help to improve maneuverability of the instrument, and to better translate a clinician's movement at the distal end of the instrument into movement of the instrument tip (e.g. by preventing coil-up outside the instrument).

Optionally, the outer sleeve may taper in a smooth manner to gradually increase its thickness towards the proximal region of the instrument. Alternatively, the outer sleeve may be configured in a stepped manner to incrementally increase its thickness towards the proximal region of the instrument. The outer sleeve may therefore include two or more sections distributed along the length of the instrument, the sections increasing in diameter from the distal region to the proximal region. This may be achieved, for example, by the outer sleeve including one or more stiffening layers extending respectively over a proximal portion of the flexible shaft and terminating respectively at an intermediate region of the flexible shaft to increase the thickness of the outer sleeve toward the proximal region of the instrument.

This arrangement may provide several advantages. Since the stiffening layers are located at a proximal portion of the flexible shaft and each terminate at an intermediate region of the flexible shaft (i.e. they do not extend over the entirety of the shaft), they may effectively stiffen the proximal portion of the instrument (i.e. reduce its flexibility) by virtue of their effect on increasing the thickness of the outer sleeve in that portion. The use of one or more stiffening layers may provide a convenient method for varying the diameter along the instrument in a step-wise manner. Further, a stepped diameter may further exaggerate the above-referenced advantages associated with providing different diameters at the portions of the instrument which sit inside or outside the scoping device, by more clearly delineating the different zones of the instrument which are configured for different purposes (e.g. insertion into the scoping device, or use outside of the scoping device).

The one or more stiffening layers may comprise any suitable material. For example, one or more of the stiffening layers may comprise a shrink-fit material (e.g. a thermoplastic such as FEP or polyester shrink). This may help to optimise the balance between improving robustness whilst maintaining a relatively small diameter. Additionally or alternatively, one of more of the stiffening layers may not comprise a shrink-fit material, e.g. it may comprise relatively thick piping. This may be useful to provide a substantially stiffer zone in a proximal region of the instrument, compared to a distal region of the instrument. Optionally, one or more of the stiffening layers may include a torque transmission layer, which may further help transfer torque along the device. For example, one or more of the stiffening layers may include a torque transmission coil (e.g. an Asahi® Torque Coil) or a braided layer (e.g. an Optinova® braided shaft). It is to be understood that this stiffening layer torque transmission coil may be in addition to the braided flexible shaft or cannula tube.

Optionally, the outer sleeve may include two or more stiffening layers. Preferably, when two or more stiffening layers are provided, they terminate at respective intermediate regions along the flexible shaft to provide a staggered variation in thickness along the length of the outer sleeve. Accordingly, the outer sleeve may include three or more sections (or 'zones') of increasing stiffness toward the proximal region. Optionally, the outer sleeve may include four or more of these sections, optionally five or more. Accordingly, an intermediate region of the instrument (which could be locatable either inside or outside the scoping device when in use) may have an intermediate thickness that can both help to prevent coil-up when it is outside the scoping device whilst also providing a relatively small profile to fit within the scoping device when needed. The provision of three or more sections may therefore help to improve the maneuverability of the instrument, i.e. to vary the extent of insertion of the instrument through the scoping device, whilst also improving rotational control of the instrument.

In some embodiments, a 'step' between a (thicker) proximal/intermediate section of the instrument and a (thinner) distal section of the instrument may act as a stopper to prevent a proximal or intermediate section of the instrument from entering the scoping device. This may help to prevent over-extension of the instrument through the scoping device.

Optionally, the outer sleeve may include different materials along its length, to increase in rigidity (decrease in flexibility) toward the proximal region of the instrument. For example, the outer sleeve may include a shrink-fit layer that extends over the distal portion of the instrument (for locating inside the scoping device in use), but which optionally does not extend over a remaining (proximal) portion of the instrument. For example, a proximal portion of the instrument may have a stiffening layer comprising a different and more rigid material than the shrink-fit layer extending over the instrument tip.

Optionally, the outer sleeve may include adjacent layers formed of complementary materials that can easily bond (e.g. under the application of heat) or otherwise adhere to each other. Providing a multi-layered outer sleeve formed of multiple materials may help to further improve its robustness and/or to improve adherence between the different materials.

Alternatively or additionally, rather than utilising a change in thickness along the length of the instrument, the outer sleeve may be configured in other manners to increase its rigidity (i.e. decrease its flexibility) towards its proximal region, e.g. by being formed of two or more different materials that are arranged to provide a higher rigidity nearer the proximal end than near the distal end. Optionally, this could be provided without requiring a decrease in thickness toward the distal end, and by instead maintaining a relatively uniform thickness along the length of the outer sleeve.

Optionally, the outer sleeve comprises a bonding layer which is configured to chemically bond to the flexible shaft under the application of heat (e.g. during heat-shrinking). This may help to further strengthen the instrument against deformation/stretching, by helping prevent relative movement of adjacent layers.

The bonding layer may comprise a polymer coating or heat-shrink material. For example, the bonding layer may comprise Pebax, which may chemically bond to an outer surface of the flexible shaft (e.g. an outer surface of an Asahi® Torque Coil). This may help to prevent fluid leakage from the flexible shaft, e.g. by reducing stretch of the coil and helping to bond strands of the torque coil together. The outer sleeve may further comprise shrink-fit layer (e.g. an FEP layer) which may clamp onto the Pebax to further improve the strength of the instrument. In variant embodiments, different materials may be used to form a chemical bond between the flexible shaft and outer sleeve.

Although the bonding layer is described here as being comprised by the outer sleeve, since the bonding layer is configured to chemically bond to the flexible shaft, the bonding layer may equally be described as being comprised by the flexible shaft rather than being comprised by the outer sleeve.

Optionally, the instrument includes an adhesive layer between the outer sleeve and the flexible shaft and/or instrument tip, for (mechanically) adhering the outer sleeve to the flexible shaft and/or instrument tip. This may help to further strengthen the attachment between the outer sleeve and the flexible shaft and/or instrument tip, to prevent deformation of the instrument. Suitable adhesives may include, for example, UV adhesives or epoxy adhesives. The adhesive layer may provide similar advantages to the above-referenced bonding layer, may not require the application of heat to adhere the different layers, and may optionally be used to adhere the outer sleeve directly to the instrument tip.

Optionally, a distal end of the flexible shaft may include an attachment collar configured to mechanically attach to a complementary interfacing section of the instrument tip.

The attachment collar may be a relatively rigid (e.g. solid metal) structure (e.g. tube) that may be attached to (e.g. by welding) or integral with a remaining (distal) section of the flexible shaft (e.g. an Asahi coil or nitinol tube) and mechanically attached to the instrument tip.

The mechanical attachment may be provided by the attachment collar having a complimentary shape, size, and/or structure to the interfacing section of the instrument tip, to form a male/female mating connection with the interfacing section. For example, the attachment collar may form a mechanical connection with the interfacing section of the instrument tip in any suitable manner, including e.g. interference attachment, press-fit attachment, rotatable (screw) attachment, or snap-fit attachment.

The mechanical attachment between the collar and the interfacing section may provide several advantages. Firstly, it can provide a convenient method for connecting the flexible shaft to the instrument tip, e.g. without requiring equipment to weld these components together. Further, since the attachment collar may form a male/female fit with the interfacing section, it may help to provide a fluid tight connection along a longer section of the junction, e.g. compared to an arrangement in which only an end surface of the instrument tip is welded to an end surface of the flexible shaft.

Similarly, the flexible shaft may include a collar at a proximal end thereof for interfacing with a complementary interfacing section of another device for receiving fluid (e.g. a fluid delivery device or interface joint).

Optionally, the distal end of the flexible shaft may be welded to the instrument tip. A welded connection may be provided in addition to an attachment collar in order to help to further strengthen the connection of the instrument tip to the instrument shaft and prevent deformation or fluid leakage. For example, the collar may be press-fit attached to the instrument tip and further tacked together with a laser weld to help prevent the risk of fluid leakage from the junction between the flexible shaft and instrument tip.

Similarly, the proximal end of the flexible shaft may be welded to another device for receiving fluid (e.g. a fluid delivery device or interface joint).

In variant embodiments, the flexible shaft may not include a collar, and the instrument tip may instead be directly attached (e.g. welded) to the flexible shaft. The instrument may include a sealing layer over the weld to seal the junction, the sealing layer being further covered by the outer sleeve. For example, the sealing layer may be formed of a polymer tube (e.g. Pebax®) which is reflowed over the weld during heat shrinking of a heat shrink layer of the outer sleeve to seal the junction.

Optionally, the flexible shaft and/or instrument tip include one or more engagement structures meshed with the outer sleeve. The engagement structure(s) may effectively grip the outer sleeve to help prevent movement of the outer sleeve relative to the flexible shaft and/or instrument tip, thereby further reinforcing their connection and helping to mitigate any stretching or deformation.

For example, the outer sleeve may include a shrink-fit layer as discussed above, which may be meshed with the one or more engagement structures. For example, the outer sleeve may include a heat-shrink layer which may be heated during manufacture to shrink against and mesh into the one or more engagement structures. By increasing the temperature at which the shrink-fit layer is applied, the strength of this attachment may be improved even further.

The one or more engagement structures may include a protrusion (e.g. rib) or depression (e.g. groove, aperture, or other indentation/recess) for meshing with the shrink-fit layer.

Optionally, the one or more engagement structures may extend along a perimeter (e.g. circumference) of the flexible shaft and/or instrument tip. For example, the one or more engagement structures extend around (at least a portion of) a circumference of the flexible shaft or an interfacing section of the instrument tip. This may effectively provide an elongate engagement structure that extends (at least in part) in a direction that is transverse to the longitudinal axis of the flexible shaft, thereby helping to better prevent stretching of the flexible shaft in a longitudinal direction.

Optionally, the flexible shaft and/or instrument tip may have an uneven surface pattern that defines the one or more engagement structures. For example, the flexible shaft may comprise a coil (e.g. an Asahi Intecc 3 layer Torque Coil) which includes ridges and grooves on its outer surface that act as engagement structures for interfacing with the shrink-fit layer.

Alternatively or additionally, the instrument may include an attachment collar which includes an engagement structure, e.g. in the form of a rib or groove.

Alternatively or additionally, the instrument tip may include the one or more engagement structures. For example, the proximal section of the instrument tip may include a first section and a second section, the first section being located proximal to the second section and being configured to interface with a distal end the flexible shaft (e.g. by interference fit, snap fit, and/or welding), and the second section having the one or more engagement structures (e.g. an indentation) for meshing with the shrink-fit layer of the outer sleeve.

In some embodiments, the distal end of the flexible shaft (e.g. a collar thereof) may be configured to provide a smooth (flush) junction with the instrument tip (e.g. by having substantially the same outer diameter as the second section). In variant embodiments, the flexible shaft may connect at a stepped junction to the instrument tip, and the stepped junction may in turn act as an engagement structure against which the outer sleeve can effectively be "locked" in place upon shrink-fitting.

Optionally, the instrument further includes a stretch limiting wire extending through the flexible shaft for limiting a maximum stretch length of the flexible shaft.

The stretch limiting wire may further help to reinforce the flexible shaft against deformation and stretching, without substantially increasing the thickness of the instrument. For example, a stretch limiting wire may have a diameter of 0.4 mm or less, preferably 0.3 mm or less, preferably 0.2 mm or less. The stretch limiting wire may be particularly useful for flexible shafts having a stretchable configuration (e.g. having a coiled structure), since the stretch limiting wire can help to prevent the flexible shaft from being propelled by the pressurised fluid to stretch distally.

In variant embodiments, the stretch limiting wire could be excluded, e.g. since other elements of the instrument may also inhibit stretching (e.g. due to the outer sleeve and/or engagement formations).

As a further advantage, in embodiments having another cable (e.g. coaxial feed cable) that extends through or next to the first fluid channel, the stretch limiting wire may help to push the coaxial cable to a side of the flexible shaft, thereby helping provide an uninterrupted fluid path down the length of the first fluid channel. Optionally, the stretch limiting wire may push the coaxial cable to a region of the flexible shaft that is aligned with a coaxial input section of the instrument tip, thereby also helping to avoid bends or curves in the coaxial cable relative to the flexible shaft near the instrument tip. The stretch limiting wire may also help to protect the electrical connections of the instrument, by helping prevent any excessive forces (e.g. stretching or bending forces) from being applied to the coaxial cable or electrical connections of the coaxial cable.

Optionally, the instrument tip is configured such that the second fluid channel decreases in diameter from a proximal end to a distal end. The second fluid channel may be configured to taper to decrease in diameter towards its distal end or may have a stepped profile to have a lower diameter in its distal end than its proximal end. The smaller diameter at the distal end may help to pressurise the fluid for piercing the tissue. For example, a distal section of the second fluid channel (e.g. a 1 mm section at the distal end of the second fluid channel) may have a diameter of 0.3 mm or less, more preferably 0.2 mm or less, whereas a proximal section of the second fluid channel (e.g. a remaining section proximal to the distal section) may have a larger diameter of 0.4 mm to 0.7 mm, e.g. 0.5 mm, which may in turn be connected to the first fluid channel having an incrementally larger diameter (e.g. the internal diameter of the flexible shaft).

Optionally, the instrument tip may include a bridging tube configured to bridge a junction between the first and second fluid channels (thereby bridging a fluid junction between the flexible shaft and the instrument tip). The bridging tube may extend through at least a distal portion of the first fluid channel, and at least a proximal portion of the second fluid channel. The bridging tube may help to stop adhesive (e.g. epoxy adhesive which may be used to seal a distal end of the coaxial cable from fluid) from blocking a fluid pathway at the distal end of the flexible shaft. Optionally, the bridging tube may be formed of a flexible material, e.g. a flexible polymer such as polyimide.

Optionally, the instrument tip includes a hypo tube forming at least a portion of the second fluid channel. The hypo tube may further help to produce a controlled water jet from the tip of the device for piercing the tissue.

A distal end of the hypo tube may comprise the nozzle, or the entirety of the hypo tube may be considered to act as the nozzle. Preferably, the hypo tube is aligned with (e.g. flush with) or proximal to a distal end of the instrument tip (e.g. a distal end of the planar body), so as not to protrude relative to the planar body. The hypo tube may be a metal tube (e.g. nitinol or stainless steel). The hypo tube may extend into the first fluid channel, and may therefore act as a bridging tube bridging a junction between the instrument tip and the flexible shaft. In contrast to a needle, the hypo tube may be fixed (non-retractable) relative to the instrument tip and may have a blunt distal end. The second fluid channel and hypo tube may provide a convenient and compact arrangement for controllably injecting fluid into tissue without requiring a needle.

In some embodiments, the hypo tube may be located (only) at a distal end of the second fluid channel, to decrease the diameter of the second fluid channel at the instrument tip relative to a (more proximal) remaining portion of the second fluid channel. This arrangement may further help to controllably pressurise fluid for injection into tissue. In alternative embodiments, the hypo tube may extend through the entirety of the instrument tip.

In other embodiments, the instrument tip may not include a hypo tube. For example, the instrument tip may instead have a bore drilled through it (e.g. through a protective hull of the instrument tip) to form the nozzle directly in the instrument tip.

Optionally, the proximal section of the instrument tip may be narrower than a distal section of the instrument tip and may terminate in one or more notches at an interface with the distal section for accommodating (seating) a distal end of the outer sleeve. This may help to provide a smoother (e.g. flush) transition between the distal end of the outer sleeve (which covers the proximal section of the instrument tip) and the distal section of the instrument tip (which is not covered by the outer sleeve). The smooth outer surface may assist with maneuverability of the device, and may help allow the flexible shaft to be as small as possible whilst retaining a preferred (e.g. larger) width at the distal end of the instrument tip. For example, the instrument tip may include a planar body having a pair of notches, the outer sleeve extending along the instrument tip up to the notches, the outer sleeve and notches being mutually sized so as to provide a substantially uniform diameter across the interface with the distal section.

Optionally, the instrument is sized for insertion through the instrument channel of a surgical scoping device having a diameter of 3.7 mm or less, more preferably 3.2 mm or less, more preferably 2.8 mm or less. For example, a distal section of the instrument for insertion through the scoping device may have a diameter of 3 mm or less, preferably 2.5 mm or less, preferably 2.1 mm or less.

Optionally, the instrument tip may have a length of 10.0 mm or less. For example, the planar body may have a length of less than 9 mm. For example, the planar body may have a length of 8 mm.

Optionally, the instrument tip may have a width of 1.9 mm or less. The instrument tip may include deviations in width along its length (e.g. having a tapering distal region to form a blade). For example, the planar body may have a maximum width of 1.8 mm. The planar body may therefore be relatively narrower than previous arrangements.

Preferably, the instrument tip may have a length that is greater than its maximum width.

Advantageously, the surgical instruments discussed herein may be used to convey fluid at a range of pressures, e.g. high pressures. For example, the instrument may be used to convey fluid at pressures of at least 100 psi, optionally at least 150 psi, optionally at least 200 psi, optionally, at least 250 psi. The specific pressures used may be selected to take into account the tissue characteristics at a target region. For example, in order to pierce mucosa (e.g. for forming initial cuts around a lesion), higher pressures may be needed than to pierce submucosa (e.g. for topping-up the lesion with fluid once the mucosa has been pierced). For example, 100 psi may provide a useful pressure for piercing submucosal tissue. Additionally, tissues in some organs (e.g. the GI tract) may be easier to pierce than others (e.g. stomach) and may therefore require lower pressures. For example, the instrument may convey fluid in a range of 250-300 psi for piercing tissue in the lower GI tract, and fluid in the range of 400-500 psi for piercing tissue in the stomach. Further, the pressure inserted into the instrument may be selected to take into account the configuration of the instrument itself, e.g. to offset any known pressure losses which may occur along the instrument, or to take into account the size of the nozzle at the instrument tip. Further, the pressures may be controlled or reduced to avoid using pressures which are too high for a particular application or body region, e.g. in order to mitigate the risk of unintended perforation.

According to a second aspect of the invention, there is provided a kit of parts for forming the electrosurgical instrument discussed above, the kit of parts including the flexible shaft, the instrument tip, and the outer sleeve. The kit of parts may include any of the features discussed above. The outer sleeve may be separate from (i.e. may not yet be applied to) the flexible shaft and the instrument tip, but may suitable for extending over the flexible shaft and proximal section of the instrument tip in the manners discussed above. Additionally, the kit of parts may include a collar (as discussed above) which may be integral with the flexible shaft or may be provided separately for attachment to another remaining portion of the flexible shaft (e.g. a cannula of the flexible shaft) e.g. by welding.

According to a third aspect of the invention, there is provided a method for forming an electrosurgical instrument for delivering pressurised fluid to a biological tissue and for delivering radiofrequency (RF) electromagnetic (EM) energy and/or microwave frequency EM energy to the biological tissue, the method comprising: providing a flexible shaft having a first fluid channel for conveying the pressurised fluid; connecting an instrument tip to a distal end of the flexible shaft, the instrument tip having a second fluid channel; and fitting an outer sleeve to extend over the flexible shaft and over a proximal section of the instrument tip to reinforce the flexible shaft and a junction between the flexible shaft and instrument tip; wherein the instrument tip comprises a planar body made of a first dielectric material separating a first conductive element on a first surface thereof from a second conductive element on a second surface thereof, the second surface facing in the opposite direction to the first surface; wherein the flexible shaft comprises a coaxial feed cable comprising an inner conductor, an outer conductor coaxial with the inner conductor, and a second dielectric material separating the inner and outer conductors, the coaxial feed cable being for conveying an RF signal and/or microwave signal; and wherein connecting the instrument tip to the distal end of the flexible shaft comprises: electrically connecting the inner conductor to the first conductive element and electrically connecting the outer conductor to the second conductive element to enable the instrument tip to receive the RF signal and/or the microwave signal; and connecting the second fluid channel to the first fluid channel to enable the second fluid channel to receive the pressurised fluid from the first fluid channel, the second fluid channel comprising a nozzle at a distal end thereof for delivering the pressurised fluid directly to the biological tissue.

The method may further include one or more steps providing any of the features/components discussed above in relation to the electrosurgical instrument and/or kit of parts.

The invention includes the combination of the aspects and preferred features described except where such a combination is clearly impermissible or expressly avoided. For example, features described above in relation to a connection at the distal end of the flexible shaft (for interfacing with the instrument tip) may optionally be applied to a connection at a proximal end of the shaft (for interfacing with a fluid delivery device or interface joint), unless such a combination is clearly impermissible or expressly avoided.

SUMMARY OF THE FIGURES

Example embodiments illustrating the principles of the invention will now be discussed with reference to the accompanying figures in which like numerals denote like elements.

FIG. 9 is a side view of the electrosurgical instrument of FIG. 2 connected to an interfacing joint and torque transfer unit.

FIG. 10 is a side view of another embodiment electrosurgical instrument connected to an interfacing joint and torque transfer unit.

DETAILED DESCRIPTION OF THE INVENTION

Aspects and embodiments of the present invention will now be discussed with reference to the accompanying figures. Further aspects and embodiments will be apparent to those skilled in the art. All documents mentioned in this text are incorporated herein by reference.

Figure 1:
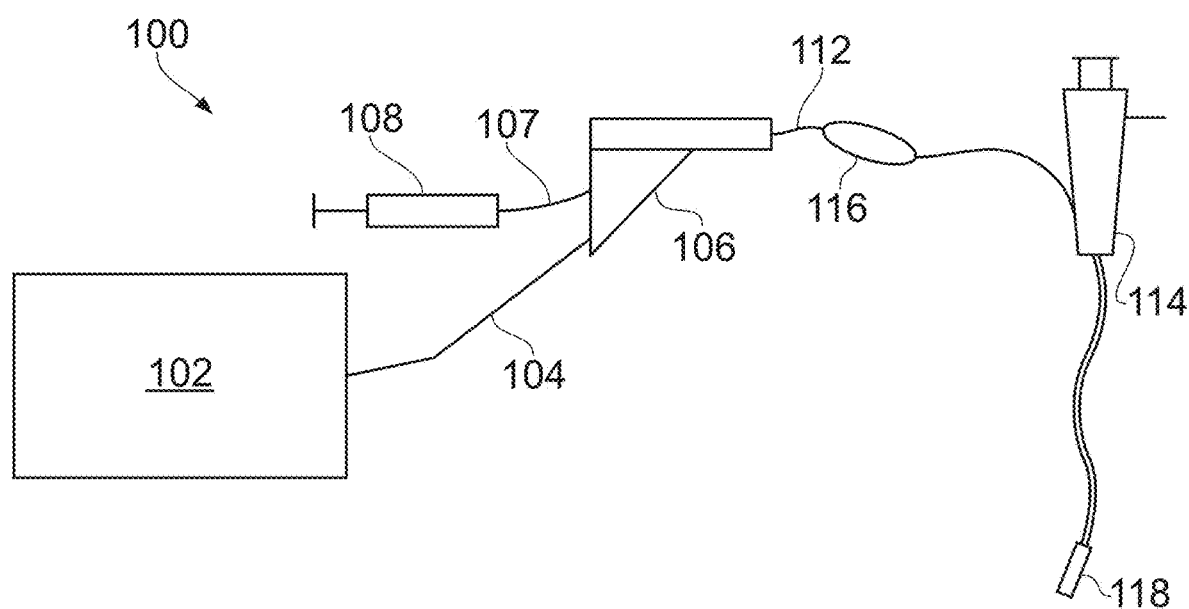
FIG. 1 is a schematic view of a complete electrosurgery system in which the present invention may be applied.

FIG. 1 is a schematic diagram of a complete electrosurgery system 100 that is capable of selectively supplying to the distal end of an invasive electrosurgical instrument any or all of RF energy, microwave energy and fluid, e.g. saline or hyaluronic acid. The system 100 comprises a generator 102 for controllable supplying electromagnetic (EM) energy. In the present embodiment, the EM energy includes RF EM energy and/or microwave frequency EM energy. A suitable generator for this purpose is described in WO 2012/076844, which is incorporated herein by reference.

The generator 102 is connected to an interface joint 106 by an interface cable 104. The interface joint 106 is also connected to receive a pressurised fluid supply from a fluid delivery apparatus 108 via a fluid supply cable 107. The function of the interface joint 106 is to combine the inputs from the generator 102 and fluid delivery device 108 into a single flexible shaft 112, which extends from the distal end of the interface joint 106. It is to be understood that the shaft 112 may form part of the interface joint 106.

The flexible shaft 112 is insertable through the entire length of an instrument (working) channel of a surgical scoping device 114. A torque transfer unit 116 may be mounted on a proximal length of the shaft 112 between the interface joint 106 and surgical scoping device 114. If present, the torque transfer unit 116 engages the shaft to permit it to be rotated within the instrument channel of the surgical scoping device 114.

The flexible shaft 112 has an electrosurgical instrument tip 118 that is shaped to pass through the instrument channel of the surgical scoping device 114 (e.g. an endoscope) and protrude (e.g. inside the patient) at the distal end of the instrument channel. The instrument tip includes an active tip for delivering RF EM energy and/or microwave EM energy into biological tissue and an aperture for delivering pressurised fluid (e.g. saline, Gelofusine, and/or hyaluronic acid with added marker dye). These combined technologies provide a unique solution for cutting and destroying unwanted tissue and the ability to seal blood vessels around the targeted area. By applying pressure to the fluid, the surgeon is able to inject the fluid between tissues layers in order to distend and mark the position of a lesion to be treated. The injection of fluid in this manner lifts and separates the tissue layers making it both easier to resect around the lesion and plane through the submucosal layer, reducing the risk of bowel wall perforation and unnecessary thermal damage to the muscle layer.

The instrument tip 118 further includes a protective hull positioned under the active tip to assist a tissue planing type resection action, again helping to protect against inadvertent perforation and ensure viability of the remaining tissue, which in turn facilitates more rapid healing and post operation recovery.

The structure of the instrument tip 118 may be particularly designed for use with a conventional steerable flexible endoscope having a working channel with an internal diameters of at least 2.2 mm and a working length of between 60 cm and 170 cm. As such the majority of the comparatively small diameter instrument is housed within the lumen of a much larger and predominantly polymer insulating device, i.e. the flexible endoscope channel. In practice, only 5 mm to 25 mm of the distal assembly protrudes from the distal end of the endoscope channel, in order not to block the field of view or adversely affect camera focusing. The protruding part of the distal assembly is the only portion of the instrument that ever makes direct contact with the patient.

At the proximal end of the endoscope working channel, which is typically held 50 cm to 80 cm from the patient, the flexible shaft 112 emerges from the working channel port and extends a further 30 cm to 100 cm to the interface joint 106. In use, the interface joint 106 is typically held by a gloved assistant throughout the procedure. The interface cable 104 is connected to the generator 102 using a QMA-type coaxial interface, which is designed to allow continuous clockwise or counter clockwise rotation. This permits the interface joint 106 to rotate with the torque transfer unit 116 under the control of the user. The assistant supports the interface joint 106 throughout the procedure in order to assist the user with sympathetic instrument rotation and fluid injection.

Figure 2:
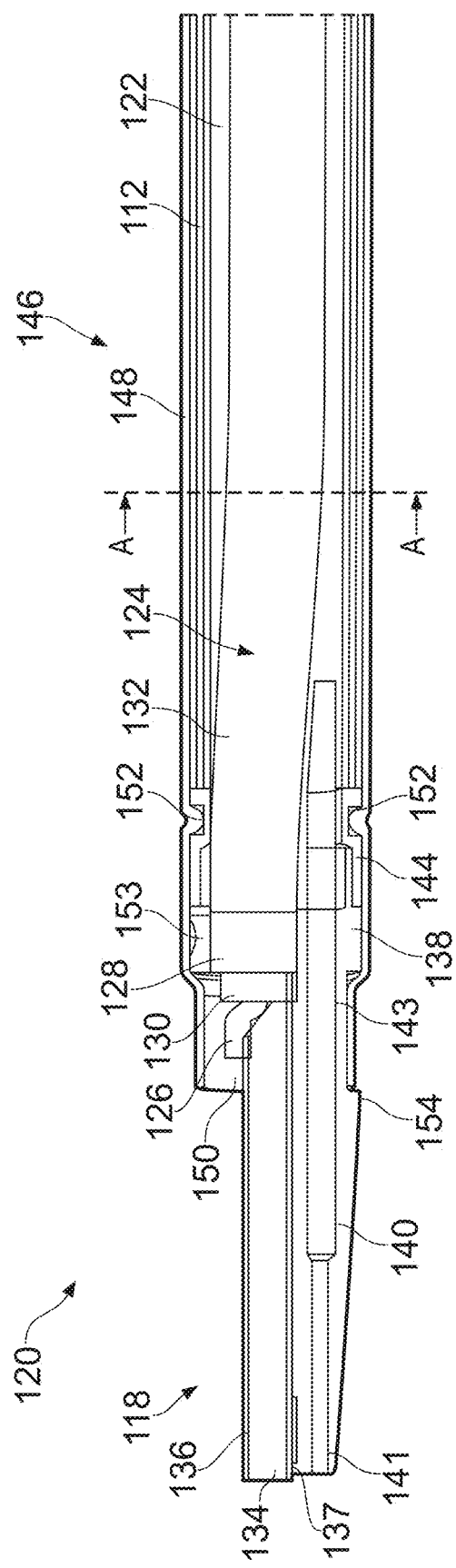
FIG. 2 is a side cross-sectional view of an electrosurgical instrument according to an embodiment of the invention.
Figure 3:
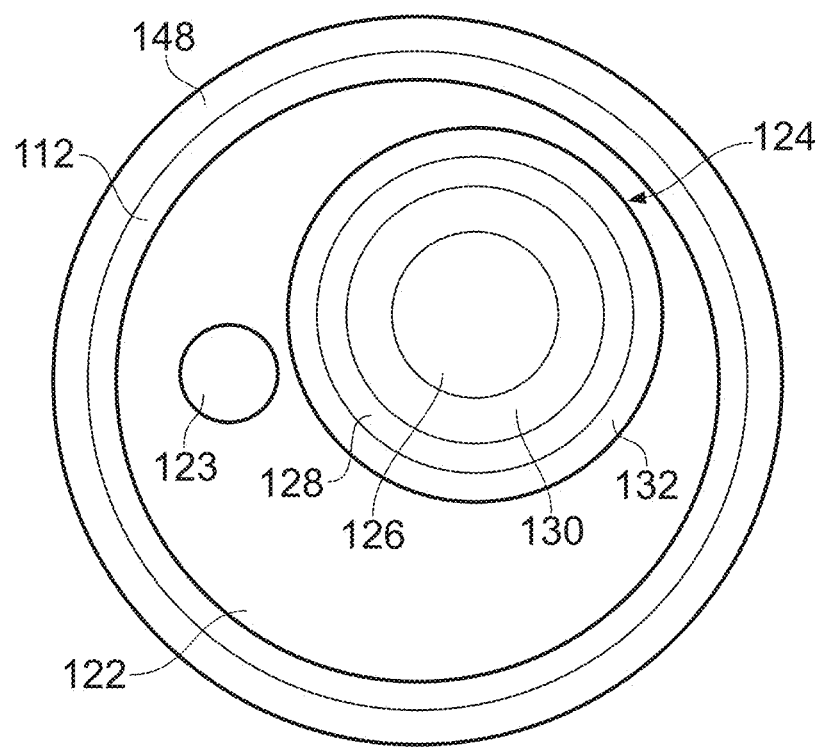
FIG. 3 is a cross-sectional view of the electrosurgical instrument of FIG. 2, as viewed along the line A-A.

FIGS. 2 to 8 show details of an electrosurgical instrument 120 that is an embodiment of the invention. In particular, FIG. 2 is a cross-sectional side view showing details of the electrosurgical instrument 120, and FIG. 3 shows another cross-sectional view of the electrosurgical instrument 120, as viewed along the line A-A shown in FIG. 2.

As can be seen from FIGS. 2 and 3, the electrosurgical instrument 120 includes a flexible shaft 112 and an instrument tip 118.

The flexible shaft 112 comprises a first fluid channel 122 for conveying pressurised fluid from a proximal end of the flexible shaft (e.g. from the interface joint 106 shown in FIG. 1) to the instrument tip 118. In this embodiment, the flexible shaft 112 includes a cannula tube and a polymer layer reflowed onto the braided tube. For example, the cannula tube may be formed of a braided tube (e.g. an Asahi torque coil) and the flexible shaft may further include a thin layer (e.g. 0.10-0.15 mm, e.g. 0.14 mm) of Pebax reflowed onto the cannula tube. In this embodiment, the flexible shaft 112 directly carries fluid therethrough, i.e. the flexible shaft 112 directly defines the first fluid channel 122. However, in variant embodiments, the flexible shaft may carry a separate lumen which defines the first fluid channel.

The flexible shaft may further include a stretch limiting wire 123 (shown in FIG. 3) extending therethrough to limit the extension of the flexible shaft 112. The stretch limiting wire 123 is not visible in FIG. 2 since it is located behind the coaxial cable 124. As shown in FIG. 3, the stretch limiting wire 123 may be arranged next to the coaxial cable 124 to offset the coaxial cable 124 to a side of the flexible shaft (e.g. toward the right side as shown in FIG. 3) to help provide an uninterrupted fluid flow path through the flexible shaft 112. In variant embodiments, the stretch limiting wire 123 may be configured to offset the coaxial cable 124 to a side of the shaft 112 that is aligned with an electrical input section 142 of the instrument tip 118 (e.g. by locating the stretch limiting wire at the lower side of the shaft from the perspective shown in FIG. 3).

The flexible shaft 112 does not include control means for controlling a retractable needle for piercing biological tissue and for conveying fluid from the first fluid channel into biological tissue.

The flexible shaft 112 further comprises a coaxial feed cable 124 (or simply "coaxial cable") for conveying an RF and/or microwave electromagnetic signal (e.g. from the generator 102 of FIG. 1) to the instrument tip 118. The coaxial feed cable 124 comprises an inner conductor 126, an outer conductor 128 coaxial with the inner conductor, a dielectric material 130 separating the inner and outer conductors. The coaxial feed cable 124 further includes an outer sheath 132 for separating the outer conductor 128 from the fluid feed channel 122.

The flexible shaft 112 is electrically connected to the instrument tip 118 to convey an EM signal from the coaxial feed cable 124 into biological tissue. In particular, the instrument tip 118 includes an active tip comprising a planar body 134 made of a dielectric material (e.g. alumina) having a first conductive element 136 and second conductive element 137 on its upper and lower surfaces, respectively. For example, the first and second conductive elements may be formed of gold.

The inner conductor 126 of the coaxial cable 124 is electrically connected to the first conductive element 136 (shown in FIGS. 4 to 6), and the outer conductor 128 of the coaxial cable 124 is electrically connected to the second conductive element 137, to enable the instrument tip to receive the EM signal. More specifically, at a distal end of the coaxial cable 124, its outer sheath 132 is removed to expose a length of the outer conductor 128. The inner conductor 126 of the coaxial cable 124 extends beyond the distal end of the outer conductor 128. The coaxial cable 124 and the instrument tip 118 are mounted relative to one another so that the protruding part of the inner conductor 126 lies on the first conductive element 136 of the active tip, while the outer conductor 128 is brought into electrical connection with the second conductive element 137 by a conductive adaptor element. The first conductive element 136 is isolated from the outer conductor 128 and the second conductive element 137 is isolated from the inner conductor 126.

Figure 4:
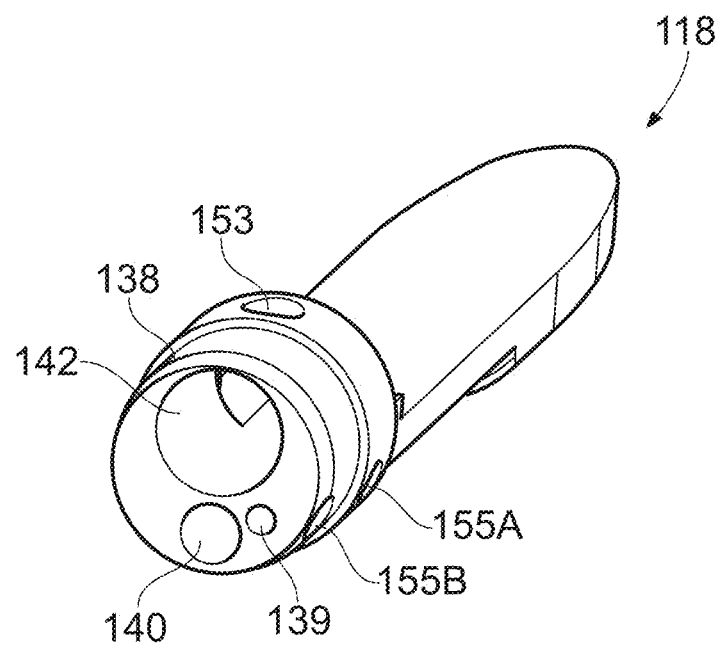
FIG. 4 is a perspective view of the instrument tip of the electrosurgical instrument of FIG. 2.
Figure 5:
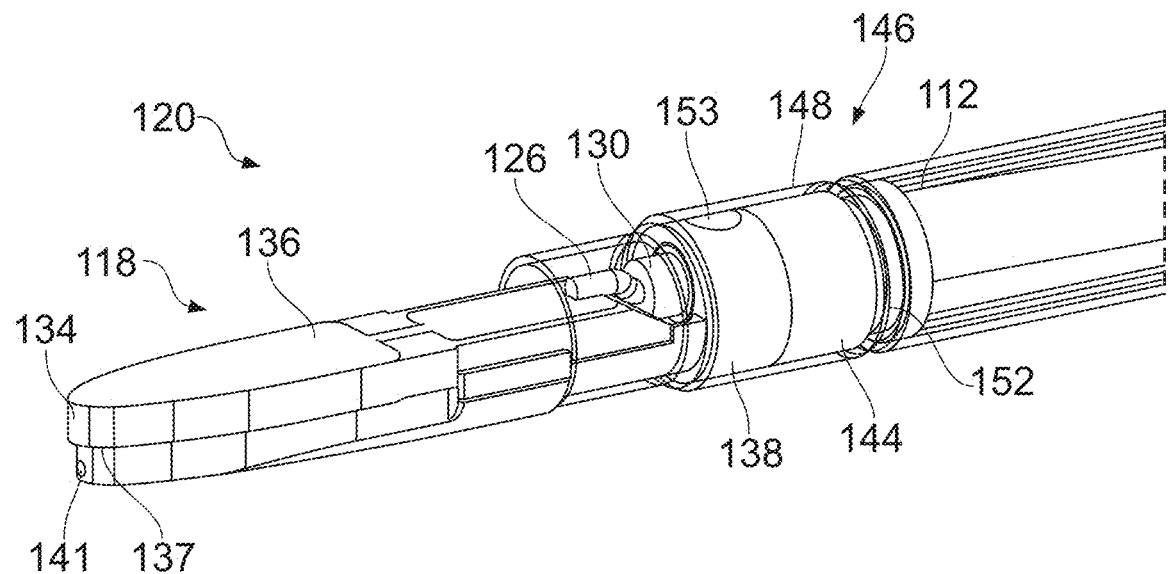
FIG. 5 is a perspective view of the electrosurgical instrument of FIG. 2, with a transparent view through the outer sleeve.
Figure 6:
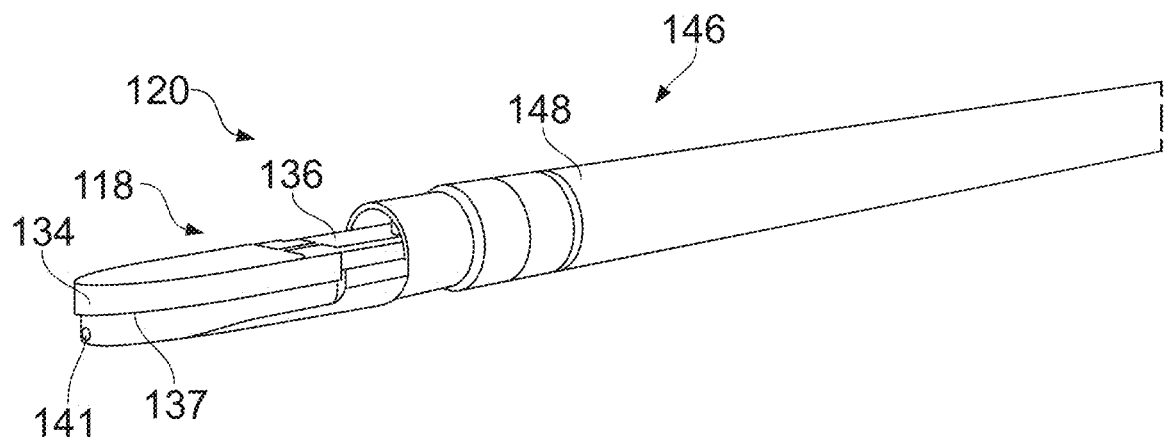
FIG. 6 is a perspective view of the electrosurgical instrument of FIG. 2.
Figure 7:
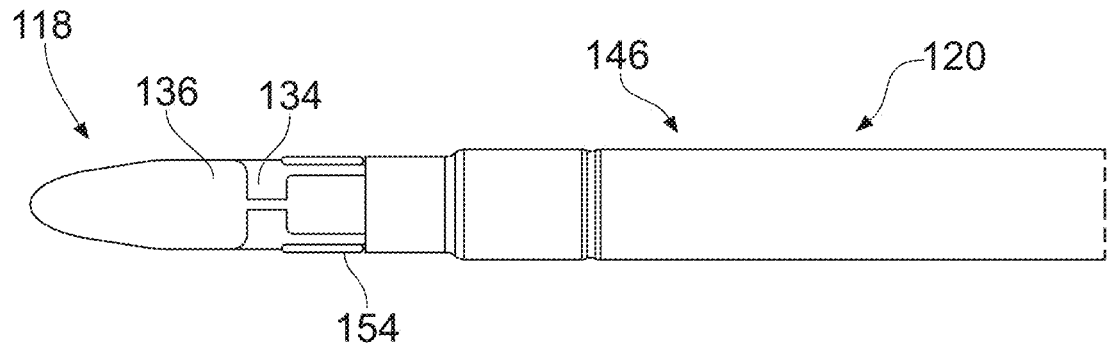
FIG. 7 is a plan view of the electrosurgical instrument of FIG. 2.
Figure 8:
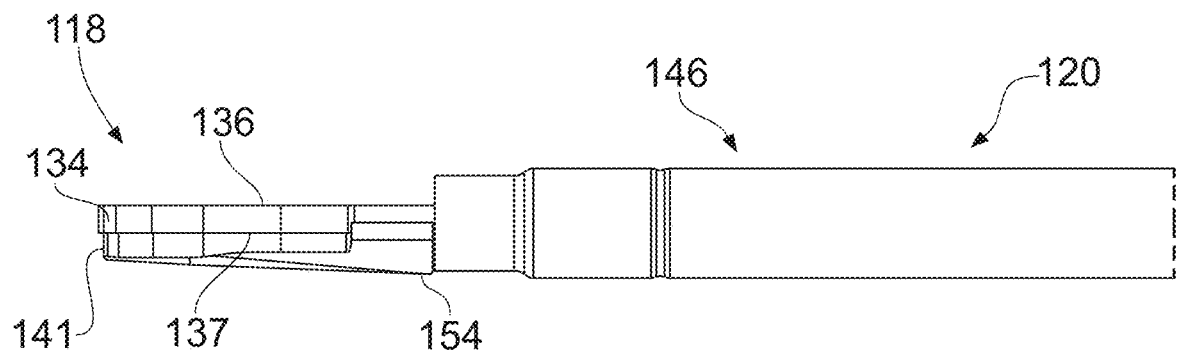
FIG. 8 is a side view of the electrosurgical instrument of FIG. 2.

FIG. 4 shows a perspective view of the instrument tip 118, including an interfacing section 138 which has a stretch wire input 139 for connecting to the stretch wire 123, an input end of a (second) fluid channel 140 for connecting to the (first) fluid channel 122 of the flexible shaft 112, and an electrical input section 142 for connecting to the coaxial cable 124 of the flexible shaft 112.

Returning to FIG. 2, the flexible shaft 112 further includes an attachment collar 144 at its distal end for connecting to the instrument tip 118. In particular, the attachment collar 144 is configured to form an interference fit with the interfacing section 138 of the instrument tip 118.

When the interfacing section 138 is mounted to the attachment collar 144, the instrument tip 118 can receive and convey the pressurised fluid and the electromagnetic signal from the flexible shaft 112 into a biological tissue.

Optionally, the instrument may further include a bridging tube 143 (e.g. polyimide tube) which extends across a junction between the first fluid channel 122 and second fluid channel 140. In this embodiment, the bridging tube 143 sits within (only) a proximal section of the second fluid channel 140, i.e. it does not extend to a distal end of the second fluid channel 140. The bridging tube 143 may help to prevent adhesive (e.g. epoxy adhesive) which is used to seal the coaxial cable 124 from fluid from blocking a fluid path between the first fluid channel 122 and second fluid channel 140.

To convey the pressurised fluid into tissue, the second fluid channel 140 extends through the instrument tip 118 to a nozzle 141. As shown in FIG. 2, the second fluid channel 140 has a stepped internal diameter, such that a distal section of the second fluid channel 140 (comprising the nozzle 141) has a smaller diameter than the proximal section of the second fluid channel 140 (comprising the bridging tube 143). The distal section of the second fluid channel 140 has the nozzle at its distal end or forms the nozzle at its distal end. In other embodiments, the instrument tip may include a hypo tube that has or forms a nozzle at its distal end. These features help the instrument tip to apply a controlled jet of pressurised fluid into tissue. Therefore, the instrument tip 118 does not require a retractable needle for piercing biological tissue and for conveying fluid from the second fluid channel 140 into biological tissue.

As shown in FIGS. 2 and 3, when the electrosurgical instrument 120 is fully assembled, it further includes an outer sleeve 146 having a shrink-fit layer 148 which extends over and grips to the flexible shaft 112 and a proximal section of the instrument tip 118. For example, the shrink-fit layer may be formed of FEP heat shrink material. The shrink-fit layer may be relatively thin, e.g. between 0.02 mm and 0.1 mm, e.g. between 0.04 mm and 0.07 mm, e.g. 0.05 mm.

The shrink-fit layer 148 extends over the instrument tip 118 to a sufficient extent as to cover the exposed portion of the inner conductor 126, i.e. covering an electrical junction between the inner conductor 126 and the first conductive element 136. The instrument includes electrical potting 150 that fills a gap between the active tip and the shrink-fit layer 148 to further encapsulate and seal this electrical junction.

Since the shrink-fit layer 148 extends over the flexible shaft 112 and over the proximal section of the instrument tip 118, it also extends over the attachment collar 144 and interfacing section 138 which join the flexible shaft 112 and the instrument tip 118. To further strengthen the attachment of the shrink-fit layer 148 to these components, the attachment collar 144 and interfacing section 138 each include a respective engagement structure for meshing with the shrink-fit layer 148.

The attachment collar 144 includes an engagement structure 152 in the form of a groove extending circumferentially around the collar 144. Further, the interfacing section 138 includes an aperture 153 which could provide an optional further engagement structure. Upon shrinking onto the surface of the flexible shaft 112 and instrument tip 118, the shrink-fit layer 148 may conform to the engagement structure 152 and aperture 153, thereby forming a stronger grip onto the device, to help prevent relative movement between the instrument tip 118 and flexible shaft 112. Additionally, the shrink-fit layer can further mesh against surface features along the length of the flexible shaft (e.g. against its coiled or braided structure).

The aperture 153 may also serve as a solder hole for attaching to the coaxial cable 124 to the interfacing section 138 of the instrument tip 118. As shown in FIG. 4, the interfacing section 138 may also include apertures 155A and 155B that may serve as weld points for connecting the stretch wire 123 to the interfacing section 138.

In this embodiment, the shrink-fit layer 148 comprises a heat shrink layer which has not been sufficiently heated in the region of the apertures 153 or 155A and 155B to mesh into the apertures. However, the heat shrink layer has been further heated in the region of the engagement structure 152 to mesh (or seep) into the circumferential groove which acts as an engagement structure 152.

The instrument tip 118 further includes a seating structure for accommodating a distal end of the outer sleeve 146. More specifically, the proximal section of the instrument tip includes a narrowed section, which terminates at a distal end in a notch 154 (also referred to as a step) having a depth substantially equal to the thickness of the outer sleeve (e.g. 0.05 mm). Upon shrinking onto the surface of the instrument tip 118, the distal end of the outer sleeve 146 is seated within the narrowed section, with a distal edge of the outer sleeve 146 aligning against the notch 154. The outer sleeve 146 can therefore form a smoother (substantially flush) boundary with the instrument tip 118.

In this embodiment, the instrument tip 118 is narrowed along the underside and side edges of its proximal section, to form a flush transition in these regions (as can be seen from FIGS. 2, and 5 to 8). However, various other configurations of narrowed sections are also possible, to accommodate the outer sleeve along different areas of the instrument tip.

As shown in FIG. 9, the outer sleeve 146 is configured to increase in thickness toward a proximal end of the instrument 120. The outer sleeve 146 includes a distal section 156 and a proximal section 158, each having different thicknesses. In use, the proximal section 158 may be located between the interface joint 106 and torque transfer unit 116, and the distal section 156 may be located (at least in part) within the surgical scoping device 114.

The distal section 156 may be suitable for insertion through surgical scoping devices having a working length of 1020 mm to 1100 mm. For example, the distal section 156 may have a working length of 1240 mm. The distal section 156 may be configured in the manner discussed above, without any further layers. For example, the distal section 156 may include (e.g. only includes) a cannula tube formed of a torque coil (e.g. Asahi torque coil) coated with a thin layer of polymer (e.g. Pebax), and a shrink-fit layer 148 e.g. comprising FEP heat shrink (e.g. 0.05 mm thick). The distal section may have a maximum outer diameter, for example, of 2.1 mm. Accordingly, the distal section may be suitable for insertion through scoping devices having an internal diameter of 2.2 mm or greater, e.g. a 2.8 mm scoping device.

The proximal section 158 may be configured similarly to the distal section 156, but further includes (e.g. only further includes) a stiffening layer to reinforce the cable between the torque transfer unit 116 and the interface joint 106. For example, the stiffening layer may comprise a braided shaft (e.g. an Optinova braided shaft) which is attached (e.g. glued) to the interface joint 106. This stiffening layer in the proximal section 158 may help to avoid coiling up and help provide better rotational control. The proximal section may have a diameter, for example, of 2.65 mm. Since the proximal section 158 is relatively thick and robust compared to the distal section 156, it may optionally omit the shrink-fit layer 148 while still being able to withstand the high pressures through the flexible shaft.

FIG. 10 shows an alternative embodiment of an instrument 220 having an outer sleeve 246 which is configured to increase in thickness towards a proximal end of the instrument. The outer sleeve 246 includes a distal section 256, a proximal section 258, and an intermediate section 260 located between the distal and proximal sections.

The distal section 256 is configured similarly to the distal section 156 of FIG. 9, but may be shorter to ensure that a majority of the distal section 256 is inserted within the scoping device when in use. For example, the distal section 256 may have a length of approximately 1155 mm, so that it is substantially fully inserted in use within a surgical scoping device having a working length of 1020 mm to 1100 mm.

The intermediate section 260 is located between the distal section 256 and the torque transfer unit 116, i.e. at a portion of the instrument which may vary between being located either within or outside of the surgical scoping device when in use. The intermediate section 260 may have an identical construction as the distal section 256, but is further reinforced relative to the distal section 258 to provide strain relief and help prevent the risk of the shaft coiling up just outside of the scoping device, while remaining thin enough to fit inside an instrument channel of the scoping device. The intermediate section 260 may also provide an advantage of allowing the device to be used with a range of surgical scoping devices (e.g. having a range of different lengths and diameters). For example, the intermediate section may have a maximum diameter of 2.5 mm (e.g. a maximum diameter of 2.25 mm), whereas the distal section may have a maximum diameter of 2.2 mm (e.g. a maximum diameter of 2.1 m).

In an embodiment, the intermediate section 260 includes a stiffening layer comprising a shrink-fit material. This can help to maintain a small profile and therefore avoid the risk of the stiffening layer affecting insertion through the scoping device when needed.

For example, the distal section may include FEP shrink-fit material (which may extend entirely between the torque transfer unit 116 and instrument tip), and the intermediate section may include the same FEP shrink-fit material in addition to one or more stiffening layers. For example, the intermediate section may include two or more layers of shrink-fit material, which are staggered along different lengths of the device to provide two or more sub-intermediate sections which increase in stiffness towards the proximal end of the instrument. For example, the intermediate section 260 may include a first stiffening layer (comprising e.g. polyester shrink fit material) extending along the entirety of the intermediate section and a second stiffening layer (comprising e.g. polyester shrink fit material) extending along a shorter length of the intermediate section, each of the materials extending up to the torque transfer unit 116. The material properties of the different layers of the outer sleeve 148 may be selected so as to provide a strong grip to each other.

The proximal section 258 is configured in an alternate manner from the proximal section 158 of FIG. 9. Rather than including a braided structure, the proximal section 258 includes stiffening layers comprising a plurality of shrink-wrap or reflowed polymer layers, but having a greater overall thickness than the intermediate section 260. The proximal section 258 may not include the same FEP shrink-fit layer which extends over the intermediate section 260 and distal section 256. For example, the proximal section 258 may (only) include two or more polyester shrink-wrap layers (e.g. each having a thickness of 0.0127 mm), covered in a relatively thick reflowed Pebax layer (e.g. having a thickness of 2.9 mm). This may provide a relatively thick reinforced section having a diameter of 2.9 mm.

Figure 11:
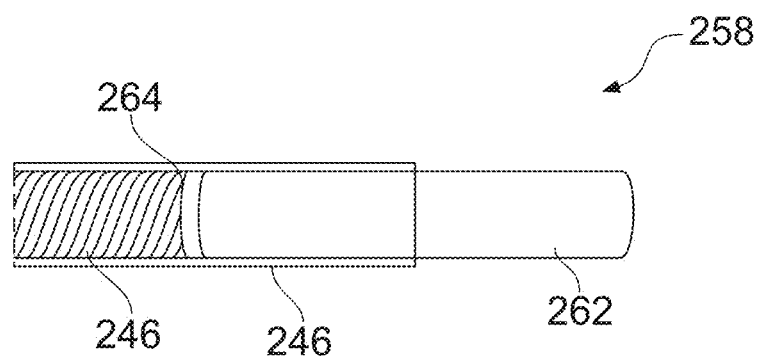
FIG. 11 is a side view showing a proximal end of a flexible shaft at its connection to an interfacing joint.
Figure 12:
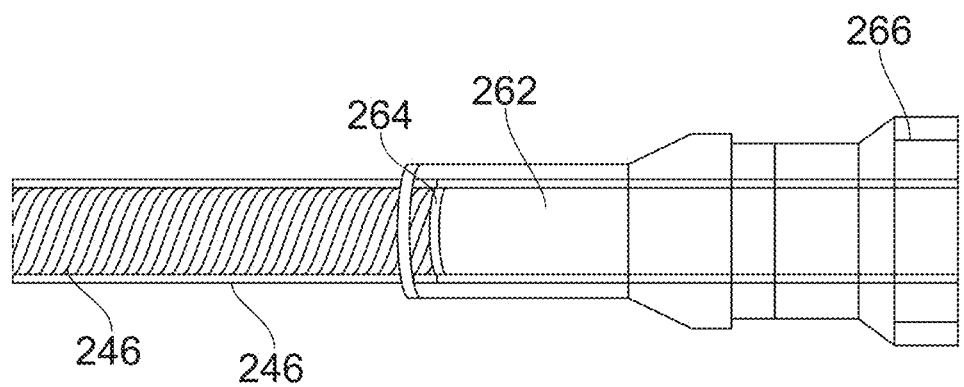
FIG. 12 is a side view showing the flexible shaft of FIG. 11 connected to the interfacing joint.

FIGS. 11 and 12 show the proximal end of the instrument in further detail according to an embodiment of the invention. This arrangement is described with reference to the outer sleeve 246 of FIG. 10, but may alternatively be applied to any other embodiment.

As shown in FIG. 11, a flexible shaft 212 is welded at its proximal end to a hypotube 262. The outer sleeve 246 extends beyond a proximal end of the flexible shaft 212, e.g. with a shrink-fit layer extending beyond a junction 264 connecting the flexible shaft 212 to the hypotube 262. As shown in FIG. 12, a sealing component 266 (e.g. Y-piece) of the interface joint 106 is attached (e.g. glued) onto the outer sleeve 246 and/or hypotube 262 to connect the flexible shaft 212 to an interface joint (e.g. the interface joint 106 of FIG. 1). The sealing component 266 overlies a proximal section of the outer sleeve and extends across the junction 264 to help further reinforce the proximal end of the instrument.

Figure 13:
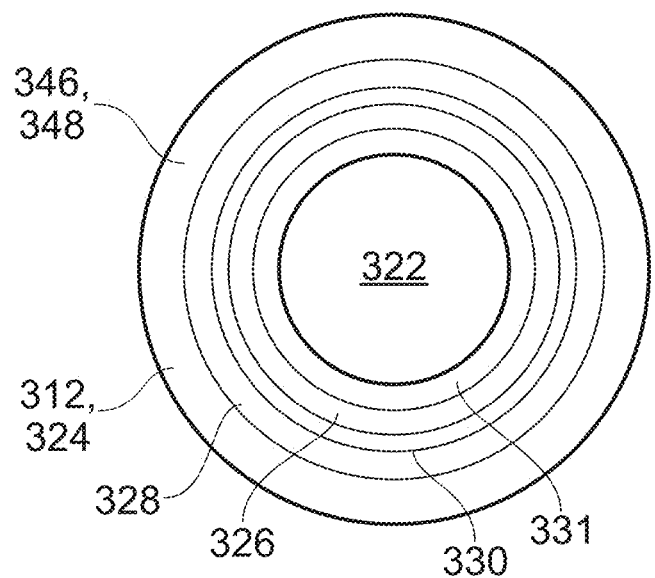
FIG. 13 is a cross-sectional view of a flexible shaft of an electrosurgical instrument according to an embodiment of the invention.
Figure 14:
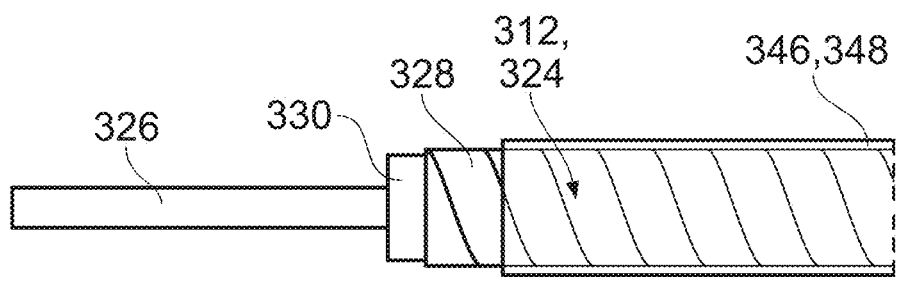
FIG. 14 is a side view of the flexible shaft of FIG. 13.
Figure 15:
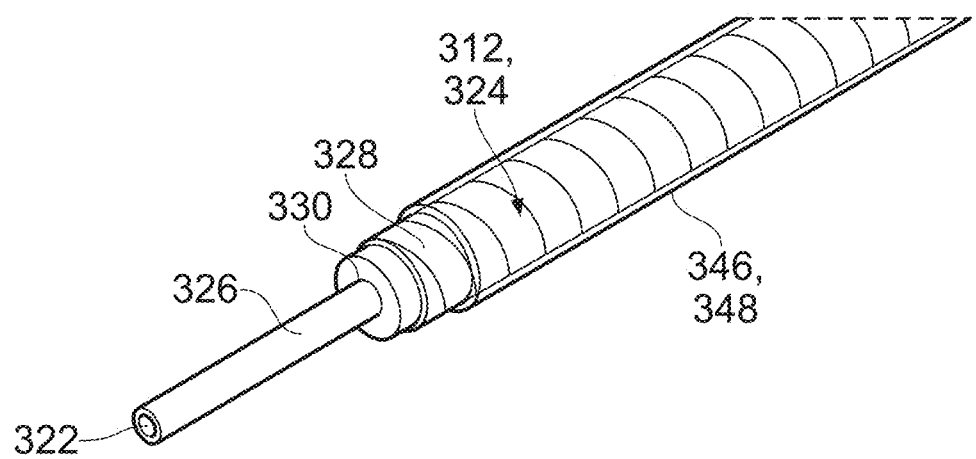
FIG. 15 is a perspective view of the flexible shaft of FIG. 13.

FIGS. 13 to 15 show details of a flexible shaft 312 of an electrosurgical instrument 320 according to an embodiment of the invention.

In contrast to the flexible shaft 112 (shown e.g. in FIG. 3), the flexible shaft 312 comprises a coaxial cable 324 which defines the fluid channel 322 through its centre.

The coaxial cable 324 includes an inner conductor 326, an outer conductor 328, and a dielectric 330 separating the inner conductor and the outer conductor. The inner conductor 326 is hollow, and an insulating layer 331 is provided on the inside of the inner conductor 326 to form the fluid channel 322.

Since the coaxial cable defines the fluid channel 322, this arrangement may help ensure that the coaxial cable does not inhibit fluid flow along the flexible shaft. Additionally, this arrangement may be made more compact than embodiments in which the coaxial cable is conveyed through or next to the fluid channel within the flexible shaft.

An outer sleeve 346 directly surrounds the coaxial cable 324. In this embodiment, the outer sleeve 346 includes a shrink-fit layer 348 formed of FEP heat-shrink material, and has a diameter of 1.85 mm when applied to the flexible shaft 312. Additionally, the inner conductor 326 comprises a super elastic nitinol tube, and has a diameter of 0.55 mm. However, in variant embodiments, the inner conductor and/or outer sleeve could be formed of other materials and/or could have different diameters, e.g. the outer sleeve could be any other outer sleeve discussed in relation to another embodiment.

Figure 16:
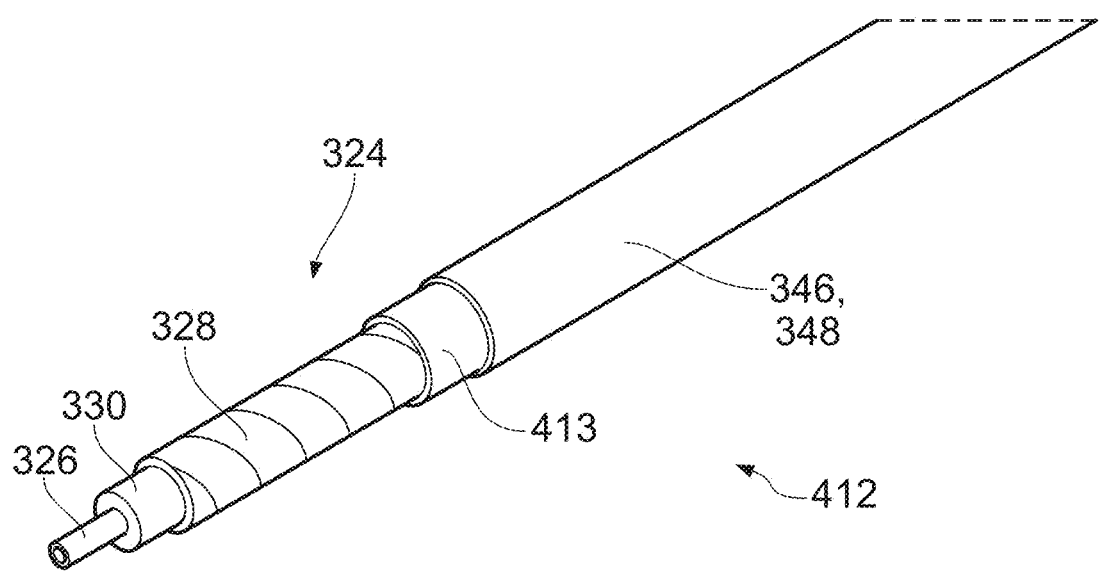
FIG. 16 is perspective view of a flexible shaft of an electrosurgical instrument according to an embodiment of the invention.
Figure 17:
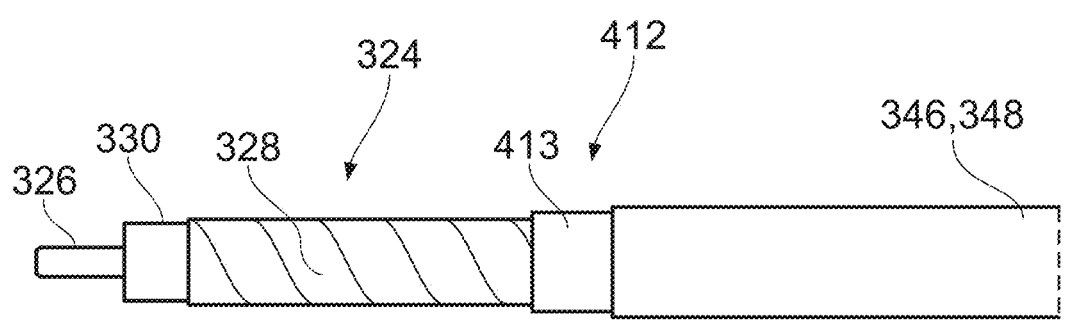
FIG. 17 is a side view of the flexible shaft of FIG. 16.

FIGS. 16 and 17 show a flexible shaft 412 having a different configuration. The flexible shaft 412 is generally similar to that of FIGS. 13 to 15, and includes similar reference numerals denoting similar features. However, the flexible shaft 412 further includes a close-fitting metallic sheath 413 (e.g. a superelastic nitinol tube) between the coaxial cable 324 and outer sleeve 348. The close-fitting metallic sheath may help to further assist in reinforcing the shaft (e.g. to prevent bursting) and may have elastic properties to help manoeuvre the distal end of the instrument, whilst maintaining a relatively small profile.

Figure 18A:
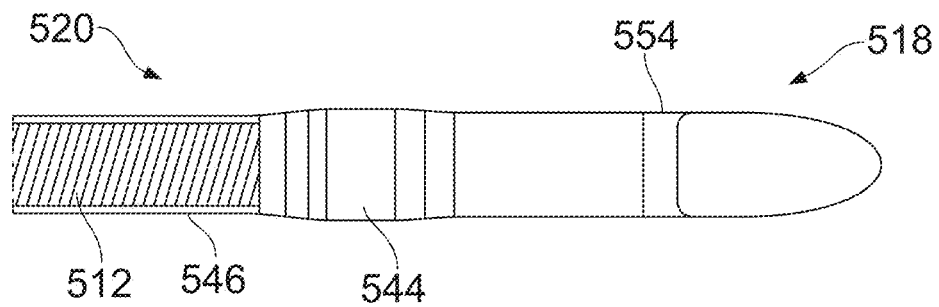
FIGS. 18A to 18C are top, side, and bottom views respectively of a distal end of an embodiment electrosurgical instrument.
Figure 18B:
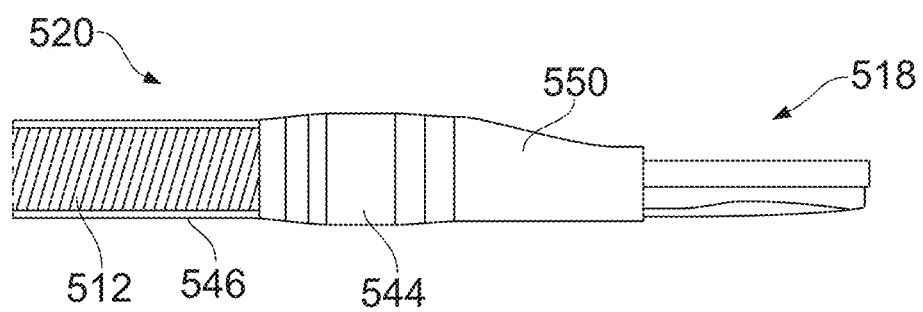
Figure 18C:
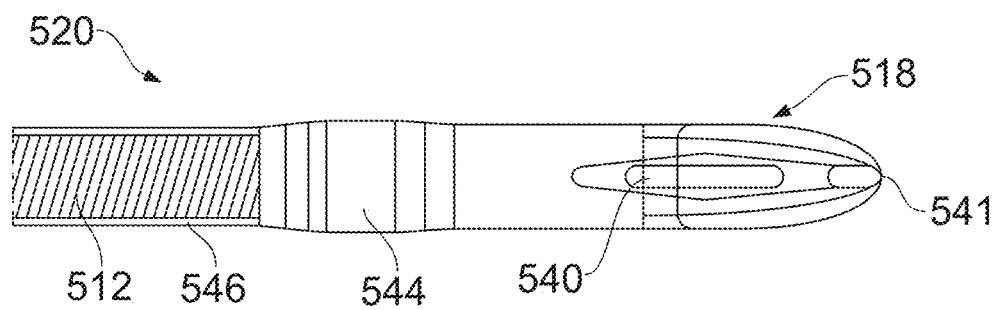

FIGS. 18A to 18C show top, side, and bottom views, respectively of an electrosurgical instrument 520 including a flexible shaft 512 and outer sleeve 546 attached to an instrument tip 518. The electrosurgical instrument 520 includes other features similar to those discussed above in relation to the electrosurgical instrument 120, and includes similar reference numerals such as an attachment collar 544, electrical potting 550, and notch 554. However, the outer sleeve 546 extends further distally over the instrument tip 518 than the outer sleeve 148. Whereas the outer sleeve 148 extends over approximately a quarter of the instrument tip's planar body, the outer sleeve 546 extends over approximately half of the instrument tip's planar body, i.e. up to a position where the instrument tip begins to taper inwardly to provide a blade-like function. By extending the outer sleeve 546 further along the instrument tip 518, its adhesion to the instrument tip can be increased, thereby further helping to prevent deformation or stretching of the flexible shaft 512 relative to the instrument tip 518.

As can be seen from FIG. 18C, a hypo tube is inserted in a distal section of the instrument tip 518 and comprises or forms a nozzle 541 at a distal end of the fluid channel 540. The hypo tube may be fixed relative to the flexible shaft 512, and may have a blunt distal end.

Figure 19:
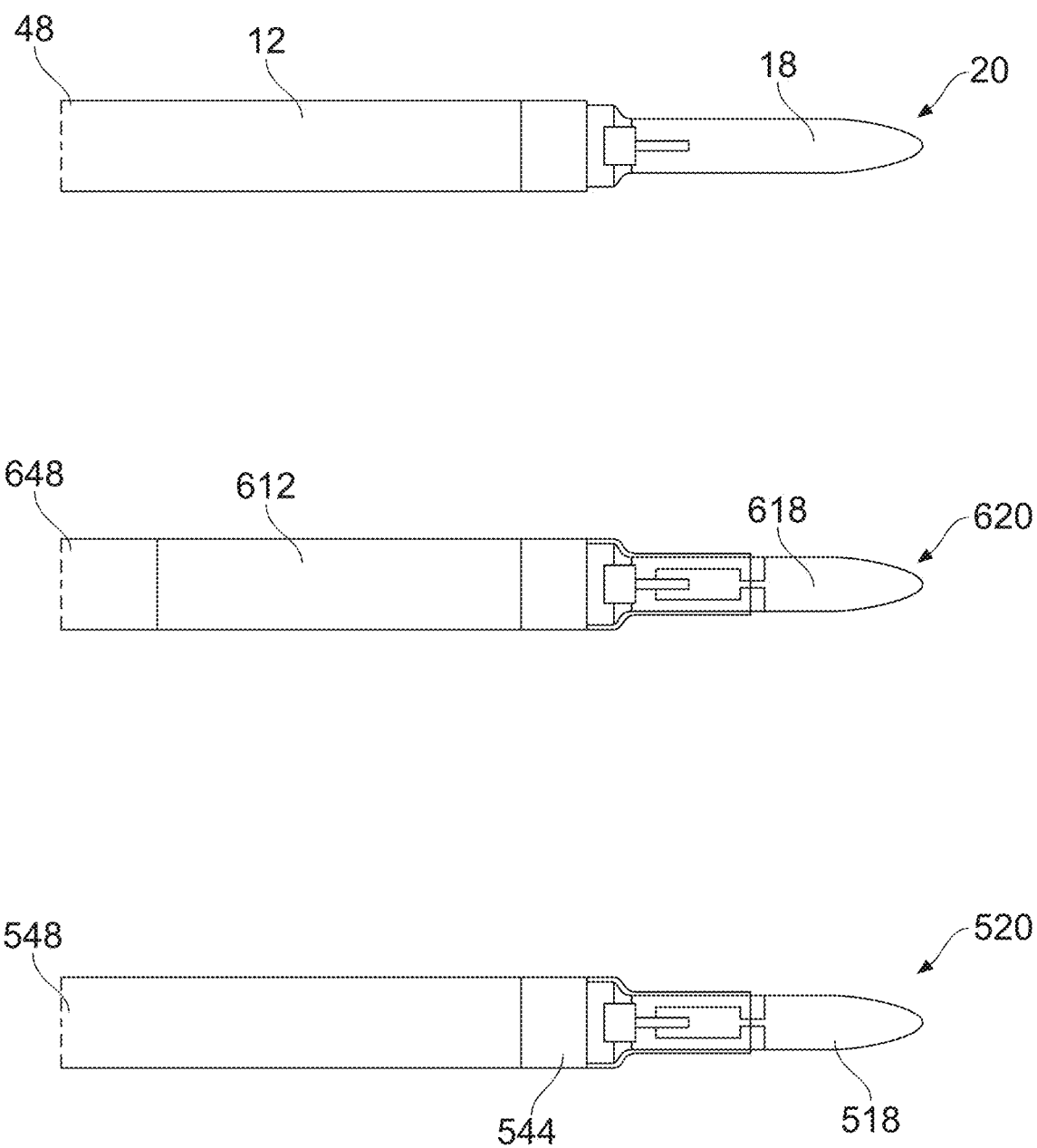
FIG. 19 is a side-by-side comparison view of three electrosurgical instruments.

FIG. 19 shows a side-by-side comparison of a non-embodiment reference electrosurgical instrument 20, the embodiment electrosurgical instrument 520 of FIGS. 18A to 18C, and another embodiment electrosurgical instrument 620.

The reference electrosurgical instrument 20 includes an instrument tip 18 having a retractable needle (not shown) and a flexible shaft 12. The flexible shaft 12 includes a cannula tube surrounding a coaxial cable, a fluid pathway, and a push rod for deploying and retracting the needle. An insulating layer 48 covers the cannula tube but does not extend onto a planar body of the instrument tip 18. Rather, the flexible shaft 12 is bonded to the active tip and to a protective hull by the application of epoxy adhesive over a portion of the coaxial cable's inner conductor that projects from the outer conductor. This epoxy adhesive also serves to form an end plug for the outer cannula tube, i.e. a fluid tight seal that means the only exit for fluid introduced at the interface joint is through a retractable needle in the instrument tip 18. The reference electrosurgical instrument may be compatible for use with scoping devices having an internal diameter of 3.8 mm, for example.

The electrosurgical instrument 620 includes a flexible shaft 612 and an instrument tip 618 that does not include a retractable needle. The flexible shaft 612 includes a cannula tube surrounding a coaxial cable and a fluid pathway, but does not include a push rod or other control means for deploying a needle. The electrosurgical instrument 620 further replaces the insulating layer 48 on the outside of the reference electrosurgical instrument 20 with an outer sleeve 648 comprising a shrink fit layer that extends over a proximal end of a planar body of the electrosurgical instrument tip 618. The electrosurgical instrument 620 is therefore able to withstand higher pressure fluids than the electrosurgical instrument 20, even at a smaller size. The instrument tip 618 is directly welded to the flexible shaft's cannula tube (not shown), and its junction is overlaid with a reflowed polymer layer (as will be discussed further in relation to FIGS. 20A to 20E). The electrosurgical instrument 620 may be compatible for use with scoping devices having an internal diameter of 3.2 mm, for example.

The electrosurgical instrument 520 is similar to the electrosurgical instrument 620, but further modifies the flexible shaft to include an attachment collar 544 to provide an interference fit with an instrument tip 518. The instrument 520 does not include the reflowed polymer layer of the instrument 620 and can therefore be made more compact than the instrument 620. This may allow the instrument size to be even further reduced, whilst maintaining the ability to withstand higher pressures. The electrosurgical instrument 520 may be compatible for use with scoping devices having an internal diameter of 2.8 mm, for example.

FIGS. 20A-20E show various stages in the assembly of an electrosurgical instrument 620.

Figure 20A:
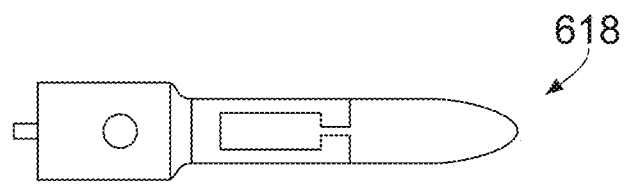
FIGS. 20A to 20E are upper views showing various stages in assembling an embodiment electrosurgical instrument that does not include an attachment collar.

FIG. 20A shows the instrument tip 618 in an initial configuration, at which stage the conductive elements have been formed on the planar body and a hypotube has been inserted into a fluid channel of the instrument tip.

Figure 20B:
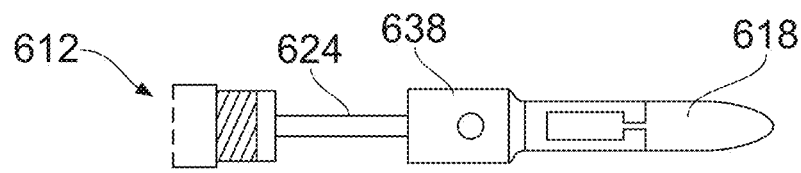

FIG. 20B shows a flexible shaft 612 having a coaxial cable 624 which is inserted through an interfacing section 638 of the instrument tip and attached to the conductive elements on the instrument tip 618.

Figure 20C:
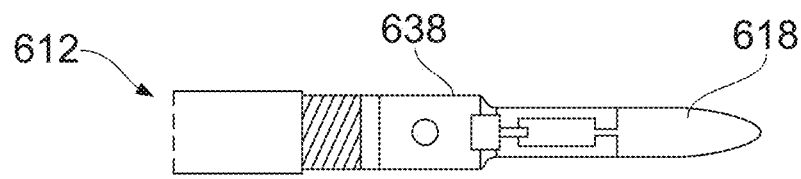

FIG. 20C shows the instrument tip 618 welded to the distal end of the flexible sleeve 612. In this embodiment, the instrument tip's interfacing section 638 is directly welded to a distal end of the flexible shaft's cannula tube. In variant embodiments, an attachment collar may instead be welded to the distal end of the flexible shaft's cannula tube, for connecting (e.g. by interference fit) to the instrument tip's interfacing section 638.

Figure 20D:
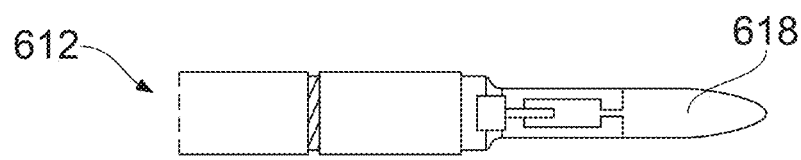
Figure 20E:
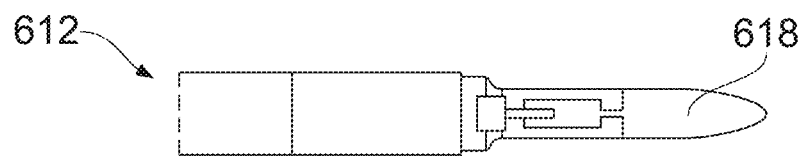

FIG. 20D shows a polymer layer (e.g. Pebax) inserted over the junction between the instrument tip 618 and flexible shaft 612. The polymer layer may be reflowed to seal the junction, as shown in FIG. 20E, and covered with a shrink-fit layer (e.g. a heat shrink layer such as FEP heat shrink).

Figure 21:
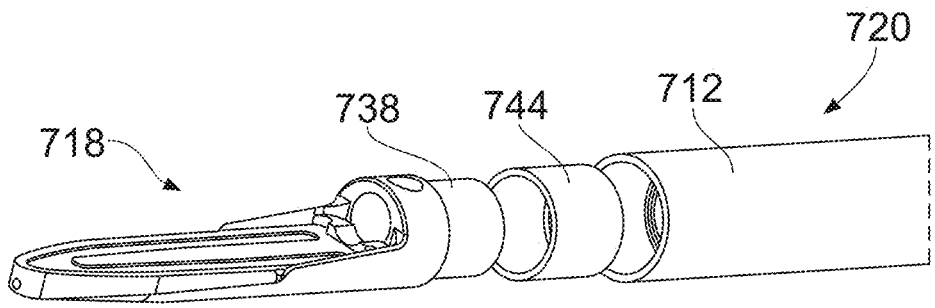
FIG. 21 is an exploded view of an embodiment electrosurgical instrument having an attachment collar.

FIG. 21 shows an exploded view of an electrosurgical instrument 720 that is another embodiment of the invention. The electrosurgical instrument 720 is generally similar to the electrosurgical instrument 120, but does not include a narrowed section terminating in a notch 154 to seat the distal end of the outer sleeve.

Further, in contrast to the electrosurgical instrument 620, the electrosurgical instrument 720 includes a flexible shaft 712 configured to connect to an instrument tip 718 via an attachment collar 744. In particular, the flexible shaft 712 includes a cannula tube which is configured to attach (e.g. by welding) to the attachment collar. The flexible shaft further includes a polymer coating (e.g. Pebax) which extends around the cannula tube and over a majority of the collar 744.

Figure 22:
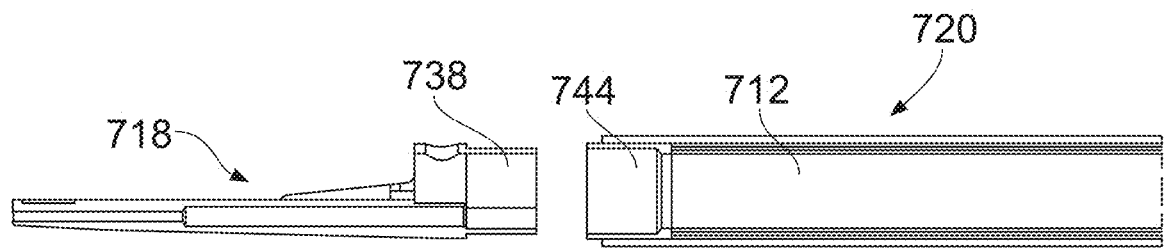
FIGS. 22 and 23 are side and perspective views, respectively, showing various stages in assembling the electrosurgical instrument of FIG. 21.

As shown in FIG. 22, the attachment collar 744 can be attached to an interfacing section 738 of the instrument tip 718 by an interference fit. Optionally, the interfacing section 738 may also be welded to the attachment collar 744 to further secure their attachment. The attachment collar may further ease assembly, e.g. compared to directly welding the instrument tip to the flexible sleeve.

Figure 23:
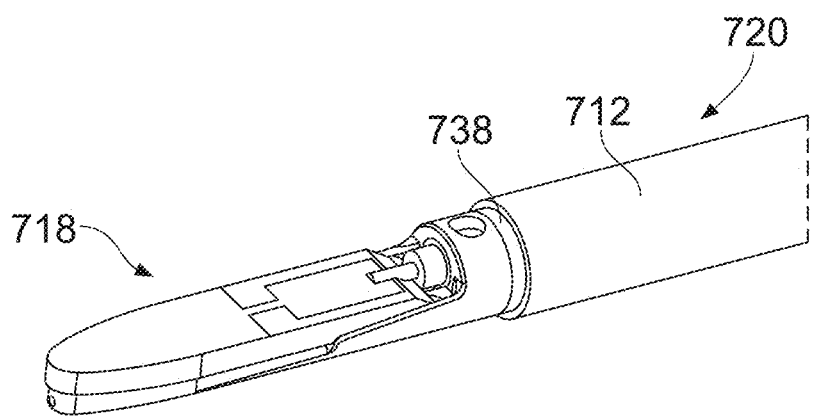

FIG. 23 shows the electrosurgical instrument 720 in a further assembled state, including the coaxial cable and active tip. An outer sleeve (not shown) may then be applied over the flexible shaft and a proximal section of the instrument tip.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

100 electrosurgery system
102 generator
104 interface cable
106 interface joint
262 hypotube
266 sealing component
120 electrosurgical instrument
112 flexible shaft
122 first fluid channel
123 stretch-limiting wire
144 collar
152 engagement structure
264 junction
118 instrument tip
140 second fluid channel
141 nozzle
143 bridging tube proximal section
154 notch
138 interfacing section
139 stretch wire input section
142 electrical input section
153 aperture
155A,B apertures active tip
134 planar body made of first dielectric material
136 first conductive element
137 second conductive element
124 coaxial feed cable
126 inner conductor
128 outer conductor
130 dielectric 132 outer sheath
331 insulating layer
146 outer sleeve
148 shrink-fit layer
156 distal section
158 proximal section
260 intermediate section
107 fluid supply cable
114 surgical scoping device
116 torque transfer unit
108 fluid delivery apparatus

The invention claimed is:

1. An electrosurgical instrument for delivering pressurised fluid to a biological tissue, and for delivering radiofrequency (RF) electromagnetic (EM) energy and/or microwave frequency EM energy to the biological tissue, the electrosurgical instrument comprising:
   a flexible shaft having a first fluid channel for conveying the pressurised fluid;
   an instrument tip connected and extending distally from to a distal end of the flexible shaft, the instrument tip having a second fluid channel for receiving the pressurised fluid from the first fluid channel, wherein the second fluid channel comprises a nozzle at a distal end thereof for delivering the pressurised fluid directly to the biological tissue, wherein the nozzle is fixed relative to the flexible shaft;
   the instrument tip comprising a planar body made of a first dielectric material separating a first conductive element on a first surface thereof from a second conductive element on a second surface thereof, the second surface facing in an opposite direction to the first surface;
   the flexible shaft comprising a coaxial feed cable comprising an inner conductor, an outer conductor coaxial with the inner conductor, and a second dielectric material separating the inner and outer conductors, the coaxial feed cable being for conveying an RF signal and/or microwave signal;
   wherein the inner conductor is electrically connected to the first conductive element and the outer conductor is electrically connected to the second conductive element to enable the instrument tip to receive the RF signal and/or the microwave signal; and
   wherein the electrosurgical instrument further includes an outer sleeve extending over the flexible shaft and a proximal section of the instrument tip to reinforce the flexible shaft and a junction between the flexible shaft and instrument tip.

2. The electrosurgical instrument according to claim 1, wherein the outer sleeve comprises a shrink-fit layer extending over the flexible shaft and the proximal section of the instrument tip to reinforce the flexible shaft and the junction between the flexible shaft and instrument tip.

3. The electrosurgical instrument of claim 2, wherein the shrink-fit layer comprises fluorinated ethylene propylene.

4. The electrosurgical instrument according to claim 1, wherein the outer sleeve extends over an entire length of the flexible shaft and beyond a proximal end of the flexible shaft.

5. The electrosurgical instrument according to claim 1, wherein the outer sleeve is configured to increase in thickness toward a proximal region of the instrument.

6. The electrosurgical instrument according to claim 5, wherein the outer sleeve includes one or more stiffening layers extending respectively over a proximal portion of the flexible shaft and terminating respectively at an intermediate region of the flexible shaft to increase the thickness of the outer sleeve toward the proximal region of the instrument.

7. The electrosurgical instrument according to claim 1, wherein one of the outer sleeve and the flexible shaft comprises a bonding layer which is configured to chemically bond to the other one of the outer sleeve and the flexible shaft under an application of heat.

8. The electrosurgical instrument according to claim 1, wherein a distal end of the flexible shaft includes an attachment collar configured to mechanically attach to a complementary interfacing section of the instrument tip.

9. The electrosurgical instrument according to claim 1, wherein the flexible shaft and/or instrument tip include one or more engagement structures meshed with the outer sleeve.

10. The electrosurgical instrument according to claim 1, further including a stretch limiting wire extending through the flexible shaft for limiting a maximum stretch length of the flexible shaft.

11. The electrosurgical instrument according to claim 1, wherein the instrument tip is configured such that the second fluid channel decreases in diameter from a proximal end to a distal end.

12. The electrosurgical instrument according to claim 1, wherein the instrument tip includes a hypo tube forming at least a portion of the second fluid channel.

13. The electrosurgical instrument according to claim 1, wherein the proximal section of the instrument tip is narrower than a distal section of the instrument tip and wherein the proximal section terminates in a notch at an interface with the distal section for accommodating a distal end of the outer sleeve.

14. The electrosurgical instrument according to claim 1, wherein the instrument is sized for insertion through the instrument channel of a surgical scoping device having a diameter of 3.7 mm or less, more preferably 3.2 mm or less, more preferably 2.8 mm or less.

15. A kit of parts for forming the electrosurgical instrument according to claim 1, the kit of parts including:
   the flexible shaft; the instrument tip; and the outer sleeve.

16. A method for forming an electrosurgical instrument for delivering pressurised fluid to a biological tissue and for delivering radiofrequency (RF) electromagnetic (EM) energy and/or microwave frequency EM energy to the biological tissue, the method comprising:
   providing a flexible shaft having a first fluid channel for conveying the pressurised fluid;
   connecting an instrument tip to a distal end of the flexible shaft to extend distally from the distal end of the flexible shaft, the instrument tip having a second fluid channel; and
   fitting an outer sleeve to extend over the flexible shaft and over a proximal section of the instrument tip to reinforce the flexible shaft and a junction between the flexible shaft and instrument tip;
   wherein the instrument tip comprises a planar body made of a first dielectric material separating a first conductive element on a first surface thereof from a second conductive element on a second surface thereof, the second surface facing in an opposite direction to the first surface;
   wherein the flexible shaft comprises a coaxial feed cable comprising an inner conductor, an outer conductor coaxial with the inner conductor, and a second dielectric material separating the inner and outer conductors, the coaxial feed cable being for conveying an RF signal and/or microwave signal; and wherein connecting the instrument tip to the distal end of the flexible shaft comprises:
- electrically connecting the inner conductor to the first conductive element and electrically connecting the outer conductor to the second conductive element to enable the instrument tip to receive the RF signal and/or the microwave signal; and
- connecting the second fluid channel to the first fluid channel to enable the second fluid channel to receive the pressurised fluid from the first fluid channel, the second fluid channel comprising a nozzle at a distal end thereof for delivering the pressurised fluid directly to the biological tissue, the nozzle being fixed relative to the flexible shaft.

* * * * *